US007935490B2

(12) United States Patent
Maertens et al.

(10) Patent No.: US 7,935,490 B2
(45) Date of Patent: May 3, 2011

(54) IMMUNODIAGNOSTIC ASSAYS USING REDUCING AGENTS

(75) Inventors: Geert Maertens, Bruges (BE); Joost Louwagie, Zwijndrecht (BE); Alfons Bosman, Opwijk (BE); Erwin Sablon, Merchtem (BE); Maan Zrein, Bondues (FR)

(73) Assignee: N.V. Innogenetics, Ghent (BE)

(*) Notice: Subject to any disclaimer, the term of this patent is extended or adjusted under 35 U.S.C. 154(b) by 0 days.

(21) Appl. No.: 11/497,259

(22) Filed: Aug. 2, 2006

(65) Prior Publication Data

US 2006/0263854 A1 Nov. 23, 2006

Related U.S. Application Data

(60) Division of application No. 09/686,964, filed on Oct. 12, 2000, now abandoned, which is a continuation of application No. PCT/EP99/02547, filed on Apr. 15, 1999.

(30) Foreign Application Priority Data

Apr. 17, 1998 (EP) .................................... 98870087

(51) Int. Cl.
   *C12Q 1/70* (2006.01)
   *G01N 33/543* (2006.01)
   *G01N 33/53* (2006.01)
(52) U.S. Cl. ........................ 435/7.1; 435/287.2; 530/350
(58) Field of Classification Search ................ 435/5, 7.1
   See application file for complete search history.

(56) References Cited

U.S. PATENT DOCUMENTS

| 4,616,078 | A |   | 10/1986 | Dimarchi |
| 5,585,258 | A |   | 12/1996 | Houghton et al. |
| 5,616,460 | A | * | 4/1997  | Figard ............................. 435/5 |
| 5,681,695 | A |   | 10/1997 | Decker et al. |
| 5,705,330 | A |   | 1/1998  | Shah et al. |
| 6,036,579 | A | * | 3/2000  | Cook et al. ....................... 451/36 |
| 6,096,319 | A |   | 8/2000  | Seidel et al. |
| 6,270,960 | B1 |  | 8/2001  | Seidel et al. |
| 6,306,579 | B1 |  | 10/2001 | Seidel et al. |

FOREIGN PATENT DOCUMENTS

| EP | 0 139 526 | | 5/1985 |
| EP | 0 346 500 | | 12/1989 |
| EP | 0 361 830 | | 4/1990 |
| JP | 06 074 956 | | 3/1994 |
| JP | 06074956 | | 3/1994 |
| WO | 91/15575 | | 10/1991 |
| WO | WO 93/00365 | | 1/1993 |
| WO | WO 94/25601 | | 11/1994 |
| WO | WO 9512677 | * | 5/1995 |
| WO | WO 9512677 A3 | | 5/1995 |
| WO | WO 95/30686 | | 11/1995 |
| WO | 96/06355 | | 2/1996 |
| WO | WO 96/00365 | | 2/1996 |
| WO | WO 96 04385 | | 2/1996 |
| WO | WO 96/13590 | | 5/1996 |
| WO | WO 96/32004 | | 10/1996 |
| WO | WO 96/41164 | | 12/1996 |
| WO | WO 97/12043 | | 4/1997 |
| WO | WO 97 12043 | | 4/1997 |
| WO | WO 97/44469 | | 11/1997 |

OTHER PUBLICATIONS

Icardi et al, J. Clinical Microbiology 1997, vol. 35, pp. 2331-2336.
Harlow et al, Antibodies: A Laboratory Manual, N.Y., Cold Spring Harbor, 1988, pp. 606-607; QR186.7.A53.
JP 60-126300 (corresponding to EP 0 139 526).
JP 9-503396(corresponding to EP WO 96/04385).
JP 9-504534 (corresponding to WO 95/12677).
JP 5-507612 (corresponding to WO 91/15575).
Masuda et al, "Efficient production of the C-terminal domain of secretory leukoprotease inhibitor as a thrombin-cleavable fusion protein in *Escherichia coli*", 1996, Protein Engineering 9, No. 101-106.
Dibella et al, "Expression and Folding of Recombinant Bovine Prethrombin-2 and Its Activation to Thrombin", 1995, Journal of Biological Chemistry, vol. 270, No. 1, 163-169.
Fischer et al. 1993, "Isolation, Renaturation, and Formation of Disulfide Bonds of Eukaryotic Proteins Expressed in *Escherichia coli* as Inclusion Bodies", Biotechnology & Bioengineering 41, No. 1, 3-13.
Cypress Diagnostics—HIV1/2 Quick Test, 1996-2002, pp. 1-5.
Cypress Diagnostics—Anti-HCV Rapid Test, 1996-2002, pp. 1-2.
Van Doorn et al, "Hepatitis C Virus Antibody Detection by a Line ImmunoAssay and (Near) Full Length Genomic RNA Detection by a New RNA-Capture Polymerase Chain Reaction", 1992—Journal of Medical Virology, 38:298-304.
Calbiochem—Empigen BB fact sheet, Cat. No. 324690, revised Jan. 4, 1999.
Lin et al, "The hepatitis C virus NS3 serine proteinase and NS4A cofactor: Establishment of a cell-free trans-processing assay", 1995, Proc Natl Acad Sci USA, vol. 92, 7622-7626.

(Continued)

*Primary Examiner* — Mary E Mosher
*Assistant Examiner* — Myron G Hill
(74) *Attorney, Agent, or Firm* — Nixon & Vanderhye P.C.

(57) ABSTRACT

The present invention relates to a solid phase immunoassay comprising on said solid phase an antigen in the presence of a reducing agent. The present invention also relates to a method for purifying a cysteine containing recombinantly expressed protein comprising at least 2, preferably 3 or 4 and even more preferably all of the following steps: (a) sulphonation of a lysate from recombinant host cells or lysis of recombinant host cells in the presence of guanidinium chloride followed by a subsequent sulphonation of the cell lysate, (b) treatment with a zwitterionic detergent, preferably after removal of the cell debris, (c) purification of the sulphonated version of the recombinant protein or purification of the sulphonated version of the recombinant protein with subsequent removal of the zwitterionic detergent, with said purification being preferably chromatography, more preferably a Ni-IMAC chromatography with said recombinant protein being a His-tagged recombinant protein, (d) desulphonation of the sulphonated version of the recombinant protein, preferably with a molar excess of DTT, (e) storage in the presence of a molar excess of DTT. The present invention also relates to novel HCV NS3 sequences as depicted in FIGS. 1-8.

17 Claims, 19 Drawing Sheets

OTHER PUBLICATIONS

Lin et al, "Hepatitis C Virus NS3 Serine Proteinase: *trans*-Cleavage Requirements and Processing Kinetics", 1994, Journal of Virology, vol. 68, No. 12, 8147-8157.

Thomson and Liang 2000 -Molecular Biology of Hepatitis C virus, p. 1 and p. 12; In: Hepatitis C (Liang, Hoofnagle, eds), Academic Press.

Majzoub et al, "Vasopressin and Oxytocin mRNA Regulation in the Rat Assessed by Hybridization with Synthetic Oligonucleotides", 1983, The Journal of Biological Chemistry, vol. 258, No. 23, 14061-14064.

File history of U.S. Appl. No. 09/686,964, retrieved from the PTO IFW on Sep. 26, 2007.

Chan et al, "Construction and selection of recombinant plasmids containing full-length complementary DNAs corresponding to rat insulins I and II", 1979, Proc Natl Acad Sci USA, vol. 76, No. 10, 5036-5040.

\* cited by examiner

Figure 1 - 1

```
            MGVAKAVDFIPVENLETTMRSPVFTDNSSPPAVPQSFQVAHLHAPTGSGKSTKVPAAYAA
NS3A5       ------------------------------------------------------------
NS3A26      ---------------------------------------------------T---V---G
NS3B7       -----------------S------------------------------------------
NS3B9       -----------------S------------------------------------------
NS3B12      -----------------S------------------------------------------
NS3B14      -----------------S------------------------------------------
NS3C1       -----------------SM-----------------------------------------
NS3C3       -----------------SM----------------T------------------------
NS3C4       -----------------SM----------------T------------------------
NS3C12      -----------------SM----------------T------------------------
NS3C16      -----------------SM----------------T------------------------
NS3D17      -----------------SM-----------------------------S-----------
NS3D18      -----------------------------------------------D------------
NS3D19      ------------------------------------------------------------
NS3HCCL19A  -----V---SM------------------------T------------------------
NS3HCCL19B  -----V---SM------------------------T------------------------
```

Figure 1 - 2

```
            QGFKVLVLNPSVAATLGFGAYMSRAHGIDPNIRTGVRTITTGSPITYSTYGKFLADGGCS
NS3A5       ------------------------------------------------------------
NS3A26      --Y---------------------------------------------------------
NS3B7       --Y------------L----KV--------------------------------------
NS3B9       --Y-----------------K---------------------------------------
NS3B12      --Y-----------------K---------------------------------------
NS3B14      --Y-M---------------K-Y-----------------T---------------R---
NS3C1       --Y-----------------K---G-------------------A---------------
NS3C3       --Y-----------------K---G-------------------A---------------
NS3C4       --Y-----------------K---G-------------------A---------------
NS3C12      --Y-----------------K---G-------------------A---------------
NS3C16      --Y-----------------K---G-------------------A---------------
NS3D17      --Y-----------------K---V-----------------------------------
NS3D18      --Y-----------------K---V-------------------------N---------
NS3D19      --Y-----------------K---V-----------------------------------
NS3HCCL19A  --Y-----------------K---V-------------------A---------------
NS3HCCL19B  --Y-----------------K---V-------------------A---------------
```

Figure 1 - 3

| | GGAYDIMICDECHSTDATSILGIGTVLDQAETAGARLVVLATAAPPGSVTVPHPNIEEVA |
|---|---|
| NS3A5 | ------------------------------------------------------------ |
| NS3A26 | --------I--------------------------------------T----------- |
| NS3B7 | --------I---------------------------------------T----------- |
| NS3B9 | --------I---------------------------------------T----------- |
| NS3B12 | --------I-----------D---------------------------T----------- |
| NS3B14 | --------I---------------------------------------T----------- |
| NS3C1 | --------I--------S-T----------------------------T----------- |
| NS3C3 | --------I--------S-T----------------------------T----------- |
| NS3C4 | --------I--------S-T----------------------------T----------- |
| NS3C12 | --------I--------S-T----------------------------T----------- |
| NS3C16 | --------I--------S-T----------------------------T----------- |
| NS3D17 | --------I----------V----------------------------T----------- |
| NS3D18 | --------I----------V----------------------------T----------- |
| NS3D19 | --------I----------V----------------------------T----------- |
| NS3HCCL19A | --------I------I-S------------------------------T----------- |
| NS3HCCL19B | --------I------I-S------------------------------T----------- |

Figure 1 - 4

```
              LSTTGEIPFYGKAIPLEAIKGGRHLIFCHSKKKCDELAAKLTALGVNAVAYYRGLDVSVI
NS3A5         ------------------------------------------------------------
NS3A26        ----------------------R-------------------------------------
NS3B7         ---------C----------------------------N-V------P-----------
NS3B9         -----------------------------------------PV----P-----------
NS3B12        -----------------------------------------V-----------------
NS3B14        ---------------------V--------------------V-----------------
NS3C1         --N------------------------T--------------V---SS--L--------
NS3C3         --N------------------------T--------------V---SS--L--------
NS3C4         --N------------------------T--------------V---SS--L--------
NS3C12        --N------------------------T--------------V---SS--L--------
NS3C16        --N------------------------T--------------V---SS--L--------
NS3D17        ---------------------------------K-----------V---I---------
NS3D18        ---------------------------------------------V---I---------
NS3D19        ---------------------------------------------QV--I---------
NS3HCCL19A    --SI----------------------------------------I-V---SGV-I----
NS3HCCL19B    --S-----------------------------------------I-V---SGF-I----
```

Figure 1 - 5

| | | |
|---|---|---|
| NS3A5 | PTSGDVVVVATDALMTGYTGDFDSVIDCNTCVTQTVDFS | (SEQ ID NO 3) |
| NS3A26 | -------------------------------------- | (SEQ ID NO 4) |
| NS3B7 | -------------------------------------- | (SEQ ID NO 5) |
| NS3B9 | ------------------------F------------- | (SEQ ID NO 6) |
| NS3B12 | ------------------------F------------- | (SEQ ID NO 7) |
| NS3B14 | ------------------------F-----------R- | (SEQ ID NO 8) |
| NS3C1 | ------------------------F----------A-- | (SEQ ID NO 9) |
| NS3C3 | ------------------------F----------A-- | (SEQ ID NO 10) |
| NS3C4 | ------------------------F------------- | (SEQ ID NO 11) |
| NS3C12 | ------------------------F------------- | (SEQ ID NO 12) |
| NS3C16 | ------------------------F------------- | (SEQ ID NO 13) |
| NS3D17 | ------------------------------------I- | (SEQ ID NO 14) |
| NS3D18 | -------------------------------------- | (SEQ ID NO 15) |
| NS3D19 | -------------------------------------- | (SEQ ID NO 16) |
| NS3HCCL19A | ------------------------F------------- | (SEQ ID NO 17) |
| NS3HCCL19B | ------------------------F------------- | (SEQ ID NO 18) |

Figure 2-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GGGGTTGCGAAGGCGGTGGACTTTGTACCCGTAGAGTCTATGGAAACCACCATGCGGTCC
CCGGTCTTTACGGATAACTCATCTCCTCCGGCCGTACCGCAGACATTCCAAGTGGCCCAT
CTACACGCCCCACTGGTAGTGGCAAGAGCACTAAGGTGCCGGCTGCATATGCAGCCCAA
GGGTACAAGGTACTTGTCCTGAACCCATCCGTTGCCGCCACCTTAGGATTCGGGGCGTAT
ATGTCTAAAGCACATGGTGTCGACCCTAACATTAGAACTGGGGTAAGGACCATCACCACG
GGCGCCCCATTACGTACTCCACCTACGGCAAGTTTCTTGCCGACGGTGGTTGCTCTGGG
GGCGCTTACGACATCATAATATGTGATGAGTGCCACTCGATTGACTCAACCTCCATCTTG
GGCATCGGCACCGTCCTGGATCAGGCGGAGACGGCTGGAGCGCGGCTTGTCGTGCTCGCC
ACTGCTACACCTCCGGGGTCGGTCACCGTGCCACATCCCAACATCGAGGAGGTGGCTCTG
TCCAGCACTGGAGAGATCCCCTTTTATGGCAAAGCCATCCCCATCGAGGTCATCAAAGGG
GGGAGGCACCTCATTTTCTGCCATTCCAAGAAGAAATGTGACGAGCTCGCCGCAAAGCTA
TCGGGCTTCGGAATCAACGCTGTAGCGTATTACCGAGGCCTTGATGTGTCCGTCATACCG
ACTAGCGGAGACGTCGTTGTTGTGGCAACAGACGCTCTAATGACGGGCTTTACCGGCGAC
TTTGACTCAGTGATCGACTGTAACACATGCGTCACCCAGACAGTCGACTTCAGCTAA
```

(SEQ ID NO 19)

Figure 2-2

```
MVRSSSQNSSDKPVAHVVANHQVEEQGIHHHHHHVDPGPMGVAKAVDFVPVESMETTMRSPVFTD
NSSPPAVPQTFQVAHLHAPTGSGKSTKVPAAYAAQGYKVLVLNPSVAATLGFGAYMSKAHGVDPN
IRTGVRTITTGAPITYSTYGKFLADGGCSGGAYDIIICDECHSIDSTSILGIGTVLDQAETAGAR
LVVLATATPPGSVTVPHPNIEEVALSSTGEIPFYGKAIPIEVIKGGRHLIFCHSKKKCDELAAKL
SGFGINAVAYYRGLDVSVIPTSGDVVVVATDALMTGFTGDFDSVIDCNTCVTQTVDFS
```

(SEQ ID NO 20)

Figure 3-1

```
ATGGTAAGATCAAGTAGTCAAAATTCGAGTGACAAGCCTGTAGCCCACGTCGTAGCAAACCACCA
AGTGGAGGAGCAGGGAATTCACCATCACCATCACCACGTGGATCCCGGGCCCATGGGGGTTGCGA
AGGCGGTGGACTTTATCCCCGTGGAGAGCCTAGAAACAACCATGAGGTCCCCGGTGTTCACAGAC
AACTCCTCCCCGCCAGCAGTGCCCCAGAGCTTCCAGGTGGCCCACCTGCATGCTCCCACCGGCAG
CGGTAAGAGCACCAAGGTCCCGGCCGCATATGCGGCTCAGGGCTACAAAGTGCTGGTGCTCAACC
CCTCCGTTGCTGCAACATTGGGCTTTGGTGCTTACATGTCCAAGGCCCATGGGATTGATCCTAAC
ATCAGGACTGGGGTAAGGACAATTACTACTGGCAGCCCCATCACGTACTCCACCTACGGCAAGTT
CCTTGCCGACGGCGGGTGCTCGGGGGTGCTTATGACATAATAATTTGTGACGAGTGCCACTCCA
CAGATGCAACATCTATTTTGGGCATCGGCACTGTCCTTGACCAAGCAGAGACTGCGGGGGCGAGA
CTGGTTGTGCTTGCCACCGCTACCCCTCCGGGCTCCGTCACTGTGCCCCATCCTAATATCGAGGA
GGTTGCTCTGTCCACCACCGGAGAGATCCCCTTTTACGGCAAGGCTATCCCCCTTGAGGCAATCA
AAGGGGGGAGACATCTCATCTTCTGCCACTCAAAGAAGAAGTGCGACGAACTCGCCGCCAAACCG
GTCGCGTTGGGTGTCAATGCCGTGGCTTACTACCGCGGCCTTGACGTGCCCGTCATCCCGACCAG
TGGCGATGTTGTCGTCGTGGCAACTGATGCTCTCATGACCGGTTTTACCGGTGACTTCGACTCGG
TGATAGACTGTAATACGTGTGTCACCCAGACAGTCGACTTCAGCTAA
```
(SEQ ID NO 21)

Figure 3-2

```
MVRSSSQNSSDKPVAHVVANHQVEEQGIHHHHHHVDPGPMGVAKAVDFIPVESLETTMRSPVFTD
NSSPPAVPQSFQVAHLHAPTGSGKSTKVPAAYAAQGYKVLVLNPSVAATLGFGAYMSKAHGIDPN
IRTGVRTITTGSPITYSTYGKFLADGGCSGGAYDIIICDECHSTDATSILGIGTVLDQAETAGAR
LVVLATATPPGSVTVPHPNIEEVALSTTGEIPFYGKAIPLEAIKGGRHLIFCHSKKKCDELAAKP
VALGVNAVAYYRGLDVPVIPTSGDVVVVATDALMTGFTGDFDSVIDCNTCVTQTVDFS
```

(SEQ ID NO 22)

Figure 4-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GCCGCGGGATTGGGCCCCCCATAGGTGTAGCAAAAGCCCTACAGTTCATACCAGTGGAA
ACCCTTAGTACGCAGGCTAGGTCTCCATCTTTCTCTGACAATTCAACTCCTCCTGCTGTC
CCACAGAGCTATCAAGTAGGGTATCTTCATGCCCCGACCGGCAGCGGTAAGAGCACAAAG
GTCCCGGCCGCTTATGTAGCACAAGGATATAATGTTCTCGTGCTGAATCCATCGGTGGCG
GCCACACTAGGCTTCGGCTCTTTCATGTCGCGTGCCTATGGGATCGACCCCAACATCCGC
ACTGGGAACCGCACCGTCACAACTGGTGCTAAACTGACCTATTCCACCTACGGTAAGTTT
CTCGCGGACGGGGGTTGCTCCGGGGGGCATATGATGTAATTATCTGTGATGAATGTCAT
GCCCAAGACGCCACTAGCATATTGGGCATAGGCACGGTCTTAGATCAGGCCGAGACGGCT
GGGGTGAGGCTGACGGTTTTAGCGACAGCAACTCCCCCAGGCAGCATCACTGTGCCACAT
TCTAACATCGAGGAAGTGGCCCTGGGCTCTGAAGGTGAGATCCCTTTCTACGGTAAGGCT
ATACCGATAGCCCTGCTCAAGGGGGGAGACACCTCGTCTTTTGCCATTCCAAGAAAAAA
TGTGATGAGCTAGCATCCAAACTCAGAGGTATGGGGCTCAACGCTGTGGCGTACTATAGG
GGTCTCGATGTTTCCGTCATACCAACAACAGGAGACGTCGTGGTCTGCGCTACTGACGCC
CTCATGACTGGATTCACTGGAGACTTCGATTCTGTCATAGACTGCAACGTGGCTGTTGAA
CAGTACGTTGACTTCAGCTAA
```

(SEQ ID NO 23)

Figure 4-2

```
MVRSSSQNSSDKPVAHVVANHQVEEQGIHHHHHHVDPGPMAAGLGPPIGVAKALQFIPVE
TLSTQARSPSFSDNSTPPAVPQSYQVGYLHAPTGSGKSTKVPAAYVAQGYNVLVLNPSVA
ATLGFGSFMSRAYGIDPNIRTGNRTVTTGAKLTYSTYGKFLADGGCSGGAYDVIICDECH
AQDATSILGIGTVLDQAETAGVRLTVLATATPPGSITVPHSNIEEVALGSEGEIPFYGKA
IPIALLKGGRHLVFCHSKKKCDELASKLRGMGLNAVAYYRGLDVSVIPTTGDVVVCATDA
LMTGFTGDFDSVIDCNVAVEQYVDFS
```

(SEQ ID NO 24)

Figure 5-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GCCGCGGGATTGGGCCCCACCATAGGTGTAGCAAAAGCCCTACAGTTCATACCAGTGGAA
ACCCTTAGCACACAGGCTAGGTCTCCATCTTTCTCTGACAATTCAACTCCTCCTGCTGTT
CCACAGAGCTATCAAGTAGGGTACCTTCATGCCCCGACCGGCAGCGGTAAGAGCACAAAG
GTCCCGGCCGCTTATGTAGCACAAGGATATACTGTTCTCGTGCTGAATCCATCGGTGGCG
GCCACACTAGGCTTCGGCTCTTTCATGTCGCGTGCCTATGGGATCGACCCCAACATCCGC
ACTGGGAACCGCACCGTTACAACTGGTGCTAAACTGACCTATTCCACCTACGGTAAGTTT
CTTGCGGATGGGGTTGCTCCGGGGGGCATATGATGTGATTATCTGTGATGAGTGTCAT
GCCCAAGACGCTACTAGCATATTGGGTATAGGCACGGTCTTAGATCAGGCCGAGACGGCT
GGGGTGAGGCTGACGGTTTTAGCGACAGCGACCCCCCAGGCAGCATCACTGTGCCACAT
TCTAACATCGAAGAAGTGGCCCTGGGCTCTGAGGGTGAGATCCCCTTCTACGGCAAGGCT
ATACCGATATCCCTGCTCAAGGGGGGAGGCACCTTATCTTTTGCCATTCCAAAAAAAAG
TGTGATAAGATAGCGTCCAAACTCAGAGGCATGGGGCTCAACGCTGTAGCGTACTATAGA
GGTCTCGATGTGTCCGTCATACCAACAACAGGAGACGTCGTAGTTTGCGCTACTGACGCC
CTCATGACTGGATACACCGGGGACTTCGATTCTGTCATAGACTGCAACGTGGCTGTTGAA
CAGTACGTTGACTTCAGCTAA
```

(SEQ ID NO 25)

Figure 5-2

MVRSSSQNSSDKPVAHVVANHQVEEQGIHHHHHHVDPGPMAAGLGPTIGVAKALQFIPVE
TLSTQARSPSFSDNSTPPAVPQSYQVGYLHAPTGSGKSTKVPAAYVAQGYTVLVLNPSVA
ATLGFGSFMSRAYGIDPNIRTGNRTVTTGAKLTYSTYGKFLADGGCSGGAYDVIICDECH
AQDATSILGIGTVLDQAETAGVRLTVLATATPPGSITVPHSNIEEVALGSEGEIPFYGKA
IPISLLKGGRHLIFCHSKKKCDKIASKLRGMGLNAVAYYRGLDVSVIPTTGDVVVCATDA
LMTGYTGDFDSVIDCNVAVEQYVDFS (SEQ ID NO 26)

Figure 6-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GGCGTGGCCAAGTCCATAGACTTCATCCCCGTTGAGACACTCGACATCGTTACGCGGTCC
CCCACCTTTAGTGACAACAGCACGCCACCGGCTGTGCCCCAGACCTATCAGGTCGGGTAC
TTGCATGCCCCAACCGGCAGCGGAAAGAGCACCAAAGTCCCCGTCGCATACGCCGCCCAG
GGGTATAAAGTGTTAGTGCTCAATCCCTCGGTGGCTGCTACCCTGGGGTTTGGAGCGTAC
CTGTCCAAGGCACACGGCATCAATCCCAACATTAGGACTGGAGTCAGGACTGTGACGACT
GGCGAAGCCATCACGTACTCCACGTATGGCAAATTCCTCGCCGATGGGGCTGCGCAGGT
GGCGCCTATGACATCATCATATGCGATGAATGCCACGCCGTGGATGCCACTACCATTCTC
GGCATCGGAACAGTCCTTGACCAAGCAGAGACAGCCGGGGTCAGGCTAACTGTGCTGGCT
ACGGCCACGCCCCCGGGTCAGTGACAACCCCCATCCCAACATAGAGGAGGTAGCCCTC
GGGCAGGAGGGTGAGACCCCCTTCTATGGGAGGCGATCCCCCTGTCTTACATCAAGGGA
GGGAGACACTTGATCTTCTGCCACTCAAAGAAAAGTGTGACGAGCTCGCGGCGGCCCTC
CGGGGCATGGGCCTGAACGCTGTGGCGTACTACAGAGGGCTCGACGTCTCCGTAATACCA
GCTCAGGGAGATGTAGTGGTCGTCGCCACCGACGCCCTCATGACGGGGTTCACTGGAGAC
TTTGACTCCGTGATCGACTGCAATGTAGCGGTCACTCAAGTTGTAGACTTCAGCTAA
```

(SEQ ID NO 27)

Figure 6-2

```
MVRSSSQNSSDKPVAHVVANHQVEEQGIHHHHHHVDPGPMGVAKSIDFIPVETLDIVTRS
PTFSDNSTPPAVPQTYQVGYLHAPTGSGKSTKVPVAYAAQGYKVLVLNPSVAATLGFGAY
LSKAHGINPNIRTGVRTVTTGEAITYSTYGKFLADGGCAGGAYDIIICDECHAVDATTIL
GIGTVLDQAETAGVRLTVLATATPPGSVTTPHPNIEEVALGQEGETPFYGRAIPLSYIKG
GRHLIFCHSKKKCDELAAALRGMGLNAVAYYRGLDVSVIPAQGDVVVVATDALMTGFTGD
FDSVIDCNVAVTQVVDFS
```

(SEQ ID NO 28)

Figure 7-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GGCGTAGCCAAATCCATTGACTTCATCCCTGTTGAATCTCTCGATATCGCCTCACGGTCA
CCCAGTTTCTCTGACAACAGCACGCCACCAGCTGTGCCTCAGTCCTACCAGGTGGGCTAT
TTGCACGCGCCAACGGGCAGCGGGAAGAGCACCAAGGTCCCTGTCGCATATGCTAGTCAG
GGGTATAAAGTACTCGTGCTAAATCCCTCTGTCGCGGCCACGCTCGGCTTCGGGGCCTAC
ATGTCCAAAGCCCACGGGATCAACCCCAACATCAGAACCGGGGTACGGACTGTGACCACC
GGGGACCCCATCACCTACTCCACTTATGGCAAGTTTCTCGCAGATGGGGCTGCTCAGCC
GGCGCCTATGATGTCATCATATGCGATGAATGCCACTCAGTGGACGCTACTACCATCCTT
GGCATTGGAACAGTCCTCGACCAGGCCGAGACCGCGGGTGCTAGGTTAGTGGTTTTAGCC
ACAGCCACGCCTCCTGGTACAGTGACAACTCCTCATAGCAACATAGAGGAGGTGGCTCTT
GGTCATGAAGGCGAGATCCCTTTCTACGGCAAGGCTATTCCCCTAGCTTTCATCAAGGGG
GGCAGACACCTAATCTTTTGCCATTCAAAGAAGAAGTGCGATGAGCTCGCGGCAGCCCTT
CGGGGCATGGGTGTCAACGCCGTTGCTTACTATAGGGGTCTCGACGTCTCTGTTATACCA
ACTCAAGGAGACGTGGTGGTCGTTGCCACCGATGCCCTAATGACTGGATACACCGGTGAC
TTTGACTCTGTTATTGACTGCAACGTTGCGGTCTCTCAAATTGTAGACTTCAGCTAA
```

(SEQ ID NO 29)

Figure 7-2

MVRSSSQNSSDKPVAHVVANHQVEEQGIHHHHHHVDPGPMGVAKSIDFIPVESLDIASRS
PSFSDNSTPPAVPQSYQVGYLHAPTGSGKSTKVPVAYASQGYKVLVLNPSVAATLGFGAY
MSKAHGINPNIRTGVRTVTTGDPITYSTYGKFLADGGCSAGAYDVIICDECHSVDATTIL
GIGTVLDQAETAGARLVVLATATPPGTVTTPHSNIEEVALGHEGEIPFYGKAIPLAFIKG
GRHLIFCHSKKKCDELAAALRGMGVNAVAYYRGLDVSVIPTQGDVVVVATDALMTGYTGD
FDSVIDCNVAVSQIVDFS (SEQ ID NO 30)

Figure 8-1

```
ATGGTAAGATCAAGTAGTCAAAATTCGAGTGACAAGCCTGTAGCCCACGTCGTAGCAAAC
CACCAAGTGGAGGAGCAGGGAATTCACCATCACCATCACCACGTGGATCCCGGGCCCATG
GGCGTAGCCAAATCCATTGACTTCATCCCCGTTGAGTCTCTCGACATCGTGACTAGGTCT
CCAAGCTTCACTGACAACAGTACACCTCCAGCCGTGCCTCAGACCTACCAAGTGGGGTAT
CTCCACGCGCCCACTGGTAGCGGGAAGAGTACCAAGGTCCCTGCAGCGTACGCCGCTCAG
GGGTACAAGGTGCTGGTACTGAACCCCTCCGTGGCTGCCACTTTGGGATTTGGGGCCTAC
ATGTCAAAAGCGCACGGAGTCAATCCCAATATCAGGACCGGGGTTCGCACGGTGAACACT
GGGGATCCCATCACCTACTCCACGTATGGCAAATTCCTCGCAGATGGAGGCTGCTCTGGA
GGCGCCTATGGCATCATAATATGCGACGAATGCCATTCGACGGACTCCACGACCATCCTC
GGCATCGGGACCGTTCTCGACCAAGCTGAGACAGCTGGAGTTAGGTTGGTGGTCTTGGCC
ACGGCGACCCCACCCGGATCTGTAACAACCCCACACCCCAACATAGAGGAGGTGGCCCTC
GGCCACGAGGGCGAAATCCCCTTCTATGGGAAGGCCATCCCTCTCTCAACCATCAAGGGA
GGACGACATCTAATCTTCTGTCATTCAAAGAAAAAGTGCGACGAGCTCGCGGTGGCCCTC
CGAGCGATGGGCCTTAACGCGGTGGCATACTACAGAGGGCTTGACGTCTCCGTGATACCA
ACACAAGGAGACGTGGTGGTCGTCGCCACCGACGCCCTCATGACAGGATATACTGGAGAC
TTCGACTCTGTGATCGACTGCAACATGGCGGTCTCTCAAATTGTAGACTTCAGCTAA
```

(SEQ ID NO 31)

Figure 8-2

```
MVRSSSQNSSDKPVAHVVANHQVEEQGIHHHHHHVDPGPMGVAKSIDFIPVESLDIVTRS
PSFTDNSTPPAVPQTYQVGYLHAPTGSGKSTKVPAAYAAQGYKVLVLNPSVAATLGFGAY
MSKAHGVNPNIRTGVRTVNTGDPITYSTYGKFLADGGCSGGAYGIIICDECHSTDSTTIL
GIGTVLDQAETAGVRLVVLATATPPGSVTTPHPNIEEVALGHEGEIPFYGKAIPLSTIKG
GRHLIFCHSKKKCDELAVALRAMGLNAVAYYRGLDVSVIPTQGDVVVVATDALMTGYTGD
FDSVIDCNMAVSQIVDFS
```

(SEQ ID NO 32)

SEQUENCE LISTING

<160> NUMBER OF SEQ ID NOS: 38

<210> SEQ ID NO 1
<211> LENGTH: 36
<212> TYPE: DNA
<213> ORGANISM: Hepatitis C virus

<400> SEQUENCE: 1
gggccccacc atggggttg cgaaggcggt ggactt                                    36

<210> SEQ ID NO 2
<211> LENGTH: 35
<212> TYPE: DNA
<213> ORGANISM: Hepatitis C virus

<400> SEQUENCE: 2
ctattagctg aaagtcgact gtctgggtga cagca                                    35

<210> SEQ ID NO 3
<211> LENGTH: 279
<212> TYPE: PRT
<213> ORGANISM: Hepatitis C virus

<400> SEQUENCE: 3

Met Gly Val Ala Lys Ala Val Asp Phe Ile Pro Val Glu Asn Leu Glu
 1               5                  10                  15

Thr Thr Met Arg Ser Pro Val Phe Thr Asp Asn Ser Ser Pro Pro Ala
             20                  25                  30

Val Pro Gln Ser Phe Gln Val Ala His Leu His Ala Pro Thr Gly Ser
         35                  40                  45

Gly Lys Ser Thr Lys Val Pro Ala Ala Tyr Ala Ala Gln Gly Phe Lys
     50                  55                  60

Val Leu Val Leu Asn Pro Ser Val Ala Ala Thr Leu Gly Phe Gly Ala
 65                  70                  75                  80

Tyr Met Ser Arg Ala His Gly Ile Asp Pro Asn Ile Arg Thr Gly Val
                 85                  90                  95

Arg Thr Ile Thr Thr Gly Ser Pro Ile Thr Tyr Ser Thr Tyr Gly Lys
            100                 105                 110

Phe Leu Ala Asp Gly Gly Cys Ser Gly Gly Ala Tyr Asp Ile Met Ile
        115                 120                 125

Cys Asp Glu Cys His Ser Thr Asp Ala Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Ala Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

```
Ala Ile Pro Leu Glu Ala Ile Lys Gly Gly Arg His Leu Ile Phe Cys
        195                 200                 205

His Ser Lys Lys Lys Cys Asp Glu Leu Ala Ala Lys Leu Thr Ala Leu
        210                 215                 220

Gly Val Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Tyr Thr Gly Asp Phe Asp Ser Val Ile Asp Cys Asn Thr Cys Val
                260                 265                 270

Thr Gln Thr Val Asp Phe Ser
        275

<210> SEQ ID NO 4
<211> LENGTH: 279
<212> TYPE: PRT
<213> ORGANISM: Hepatitis C virus

<400> SEQUENCE: 4

Met Gly Val Ala Lys Ala Val Asp Phe Ile Pro Val Glu Asn Leu Glu
1               5                   10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Gly Ser
        35                  40                  45

Gly Lys Ser Thr Thr Val Pro Ala Val Tyr Ala Ala Gln Gly Phe Lys
    50                  55                  60

Val Leu Val Leu Asn Pro Ser Val Ala Ala Thr Leu Gly Phe Gly Ala
65                  70                  75                  80

Tyr Met Ser Arg Ala His Gly Ile Asp Pro Asn Ile Arg Thr Gly Val
                85                  90                  95

Arg Thr Ile Thr Thr Gly Ser Pro Ile Thr Tyr Ser Thr Tyr Gly Lys
            100                 105                 110

Phe Leu Ala Asp Gly Gly Cys Ser Gly Gly Ala Tyr Asp Ile Ile Ile
        115                 120                 125

Cys Asp Glu Cys His Ser Thr Asp Ala Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg Arg Leu Ile Phe Cys
        195                 200                 205

His Ser Lys Lys Lys Cys Asp Glu Leu Ala Ala Lys Leu Thr Ala Leu
        210                 215                 220

Gly Val Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Tyr Thr Gly Asp Phe Asp Ser Val Ile Asp Cys Asn Thr Cys Val
                260                 265                 270

Thr Gln Thr Val Asp Phe Ser
        275
```

-continued

<210> SEQ ID NO 5
<211> LENGTH: 279
<212> TYPE: PRT
<213> ORGANISM: Hepatitis C virus

<400> SEQUENCE: 5

```
Met Gly Val Ala Lys Ala Val Asp Phe Ile Pro Val Glu Ser Leu Glu
 1               5                  10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Gly Ser
        35                  40                  45

Gly Lys Ser Thr Lys Val Pro Ala Ala Tyr Ala Gly Gln Gly Tyr Lys
    50                  55                  60

Val Leu Val Leu Asn Pro Ser Val Ala Ala Thr Leu Gly Leu Gly Ala
65                  70                  75                  80

Tyr Met Ser Lys Val His Gly Ile Asp Pro Asn Ile Arg Thr Gly Val
                85                  90                  95

Arg Thr Ile Thr Thr Gly Ser Pro Ile Thr Tyr Ser Thr Tyr Gly Lys
            100                 105                 110

Phe Leu Ala Asp Gly Gly Cys Ser Gly Gly Ala Tyr Asp Ile Ile Ile
        115                 120                 125

Cys Asp Glu Cys His Ser Thr Asp Ala Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Cys Gly Lys
            180                 185                 190

Ala Ile Pro Leu Glu Ala Ile Lys Gly Gly Arg His Leu Ile Phe Cys
        195                 200                 205

His Ser Lys Lys Lys Cys Asp Glu Leu Ala Ala Asn Leu Val Ala Leu
    210                 215                 220

Gly Val Asn Pro Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Tyr Thr Gly Asp Phe Asp Ser Val Ile Asp Cys Asn Thr Cys Val
            260                 265                 270

Thr Gln Thr Val Asp Phe Ser
        275
```

<210> SEQ ID NO 6
<211> LENGTH: 279
<212> TYPE: PRT
<213> ORGANISM: Hepatitis C virus

<400> SEQUENCE: 6

```
Met Gly Val Ala Lys Ala Val Asp Phe Ile Pro Val Glu Ser Leu Glu
 1               5                  10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Gly Ser
        35                  40                  45
```

```
Gly Lys Ser Thr Lys Val Pro Ala Ala Tyr Ala Ala Gln Gly Tyr Lys
        50                  55                  60

Val Leu Val Leu Asn Pro Ser Val Ala Ala Thr Leu Gly Phe Gly Ala
 65                  70                  75                  80

Tyr Met Ser Lys Ala His Gly Ile Asp Pro Asn Ile Arg Thr Gly Val
                 85                  90                  95

Arg Thr Ile Thr Thr Gly Ser Pro Ile Thr Tyr Ser Thr Tyr Gly Lys
                100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Ala Thr Ser Ile Leu Gly Ile Gly
130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Ile Phe Cys
            195                 200                 205

His Ser Lys Lys Lys Cys Asp Glu Leu Ala Ala Lys Pro Val Ala Leu
        210                 215                 220

Gly Val Asn Ala Val Ala Tyr Tyr Arg Gly Leu Asp Val Pro Val Ile
225                 230                 235                 240

Pro Thr Ser Gly Asp Val Val Val Ala Thr Asp Ala Leu Met Thr
                245                 250                 255

Gly Phe Thr Gly Asp Phe Asp Ser Val Ile Asp Cys Asn Thr Cys Val
            260                 265                 270

Thr Gln Thr Val Asp Phe Ser
        275

<210> SEQ ID NO 7
<211> LENGTH: 279
<212> TYPE: PRT
<213> ORGANISM: Hepatitis C virus

<400> SEQUENCE: 7

Met Gly Val Ala Lys Ala Val Asp Phe Ile Pro Val Glu Ser Leu Glu
 1               5                  10                  15

Thr Thr Met Arg Ser Pro Val Phe Thr Asp Asn Ser Ser Pro Pro Ala
             20                  25                  30

Val Pro Gln Ser Phe Gln Val Ala His Leu His Ala Pro Thr Gly Ser
         35                  40                  45

Gly Lys Ser Thr Lys Val Pro Ala Ala Tyr Ala Ala Gln Gly Tyr Lys
        50                  55                  60

Val Leu Val Leu Asn Pro Ser Val Ala Ala Thr Leu Gly Phe Gly Ala
 65                  70                  75                  80

Tyr Met Ser Lys Ala His Gly Ile Asp Pro Asn Ile Arg Thr Gly Val
                 85                  90                  95

Arg Thr Ile Thr Thr Gly Ser Pro Ile Thr Tyr Ser Thr Tyr Gly Lys
                100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Ala Thr Ser Ile Leu Asp Ile Gly
130                 135                 140
```

```
Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Ile Phe Cys
        195                 200                 205

His Ser Lys Lys Lys Cys Asp Glu Leu Ala Ala Lys Leu Val Ala Leu
    210                 215                 220

Gly Val Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Phe Thr Gly Asp Phe Asp Ser Val Ile Asp Cys Asn Thr Cys Val
            260                 265                 270

Thr Gln Thr Val Asp Phe Ser
        275

<210> SEQ ID NO 8
<211> LENGTH: 279
<212> TYPE: PRT
<213> ORGANISM: Hepatitis C virus

<400> SEQUENCE: 8

Met Gly Val Ala Lys Ala Val Asp Phe Ile Pro Val Glu Ser Leu Glu
1               5                   10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Gly Ser
        35                  40                  45

Gly Lys Ser Thr Lys Val Pro Ala Ala Tyr Ala Ala Gln Gly Tyr Lys
    50                  55                  60

Met Leu Val Leu Asn Pro Ser Val Ala Ala Thr Leu Gly Phe Gly Ala
65                  70                  75                  80

Tyr Met Ser Lys Ala Tyr Gly Ile Asp Pro Asn Ile Arg Thr Gly Val
                85                  90                  95

Arg Thr Ile Thr Thr Gly Ser Pro Thr Thr Tyr Ser Thr Tyr Gly Lys
            100                 105                 110

Phe Leu Ala Asp Gly Gly Arg Ser Gly Gly Ala Tyr Asp Ile Ile Ile
        115                 120                 125

Cys Asp Glu Cys His Ser Thr Asp Ala Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Val Phe Cys
        195                 200                 205

His Ser Lys Lys Lys Cys Asp Glu Leu Ala Ala Lys Leu Val Ala Leu
    210                 215                 220

Gly Val Asn Ala Val Ala Tyr Tyr Arg Gly Leu Asp Val Ser Val Ile
225                 230                 235                 240
```

Pro Thr Ser Gly Asp Val Val Val Ala Thr Asp Ala Leu Met Thr
            245                 250                 255

Gly Phe Thr Gly Asp Phe Asp Ser Val Ile Asp Cys Asn Thr Cys Val
                260                 265                 270

Thr Gln Thr Val Asp Phe Arg
        275

<210> SEQ ID NO 9
<211> LENGTH: 279
<212> TYPE: PRT
<213> ORGANISM: Hepatitis C virus

<400> SEQUENCE: 9

Met Gly Val Ala Lys Ala Val Asp Phe Ile Pro Val Glu Ser Met Glu
  1               5                  10                  15

Thr Thr Met Arg Ser Pro Val Phe Thr Asp Asn Ser Ser Pro Pro Ala
                 20                  25                  30

Val Pro Gln Thr Phe Gln Val Ala His Leu His Ala Pro Thr Gly Ser
             35                  40                  45

Gly Lys Ser Thr Lys Val Pro Ala Ala Tyr Ala Ala Gln Gly Tyr Lys
         50                  55                  60

Val Leu Val Leu Asn Pro Ser Val Ala Ala Thr Leu Gly Phe Gly Ala
 65                  70                  75                  80

Tyr Met Ser Lys Ala His Gly Ile Asp Pro Gly Ile Arg Thr Gly Val
                 85                  90                  95

Arg Thr Ile Thr Thr Gly Ala Pro Ile Thr Tyr Ser Thr Tyr Gly Lys
                100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Ser Thr Thr Ile Leu Gly Ile Gly
130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Asn Thr Gly Glu Ile Pro Phe Tyr Gly Lys
            180                 185                 190

Ala Ile Pro Leu Glu Thr Ile Lys Gly Gly Arg His Leu Ile Phe Cys
        195                 200                 205

His Ser Lys Lys Lys Cys Asp Glu Leu Ala Ala Lys Leu Ser Ser Leu
210                 215                 220

Gly Leu Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
            245                 250                 255

Gly Phe Thr Gly Asp Phe Asp Ser Val Ile Asp Cys Asn Thr Cys Ala
                260                 265                 270

Thr Gln Thr Val Asp Phe Ser
        275

<210> SEQ ID NO 10
<211> LENGTH: 279
<212> TYPE: PRT
<213> ORGANISM: Hepatitis C virus

<400> SEQUENCE: 10

Met Gly Val Ala Lys Ala Val Asp Phe Ile Pro Val Glu Ser Met Glu

```
                1               5                   10                  15
Thr Thr Met Arg Ser Pro Val Phe Thr Asp Asn Ser Ser Pro Pro Ala
                    20                  25                  30

Val Pro Gln Thr Phe Gln Val Ala His Leu His Ala Pro Thr Gly Ser
                35                  40                  45

Ser Lys Ser Thr Lys Val Pro Ala Ala Tyr Ala Ala Gln Gly Tyr Lys
            50                  55                  60

Val Leu Val Leu Asn Pro Ser Val Ala Ala Thr Leu Gly Phe Gly Ala
65                  70                  75                  80

Tyr Met Ser Lys Ala His Gly Ile Asp Pro Gly Ile Arg Thr Gly Val
                    85                  90                  95

Arg Thr Ile Thr Thr Gly Ala Pro Ile Thr Tyr Ser Thr Tyr Gly Lys
                100                 105                 110

Phe Leu Ala Asp Gly Gly Cys Ser Gly Gly Ala Tyr Asp Ile Ile Ile
                115                 120                 125

Cys Asp Glu Cys His Ser Thr Asp Ser Thr Thr Ile Leu Gly Ile Gly
                130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                    165                 170                 175

Glu Glu Val Ala Leu Ser Asn Thr Gly Glu Ile Pro Phe Tyr Gly Lys
                180                 185                 190

Ala Ile Pro Leu Glu Thr Ile Lys Gly Gly Arg His Leu Ile Phe Cys
                    195                 200                 205

His Ser Lys Lys Lys Cys Asp Glu Leu Ala Ala Lys Leu Ser Ser Leu
            210                 215                 220

Gly Leu Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                    245                 250                 255

Gly Phe Thr Gly Asp Phe Asp Ser Val Ile Asp Cys Asn Thr Cys Ala
                260                 265                 270

Thr Gln Thr Val Asp Phe Ser
                275

<210> SEQ ID NO 11
<211> LENGTH: 279
<212> TYPE: PRT
<213> ORGANISM: Hepatitis C virus

<400> SEQUENCE: 11

Met Gly Val Ala Lys Ala Val Asp Phe Ile Pro Val Glu Ser Met Glu
1               5                   10                  15

Thr Thr Met Arg Ser Pro Val Phe Thr Asp Asn Ser Ser Pro Pro Ala
                    20                  25                  30

Val Pro Gln Thr Phe Gln Val Ala His Leu His Ala Pro Thr Gly Ser
                35                  40                  45

Gly Lys Ser Thr Lys Val Pro Ala Ala Tyr Ala Ala Gln Gly Tyr Lys
            50                  55                  60

Val Leu Val Leu Asn Pro Ser Val Ala Ala Thr Leu Gly Phe Gly Ala
65                  70                  75                  80

Tyr Met Ser Lys Ala His Gly Ile Asp Pro Gly Ile Arg Thr Gly Val
                    85                  90                  95

Arg Thr Ile Thr Thr Gly Ala Pro Ile Thr Tyr Ser Thr Tyr Gly Lys
```

```
            100                 105                 110
Phe Leu Ala Asp Gly Gly Cys Ser Gly Gly Ala Tyr Asp Ile Ile Ile
            115                 120                 125

Cys Asp Glu Cys His Ser Thr Asp Ser Thr Thr Ile Leu Gly Ile Gly
        130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Asn Thr Gly Glu Ile Pro Phe Tyr Gly Lys
            180                 185                 190

Ala Ile Pro Leu Glu Thr Ile Lys Gly Gly Arg His Leu Ile Phe Cys
        195                 200                 205

His Ser Lys Lys Lys Cys Asp Glu Leu Ala Ala Lys Leu Ser Ser Leu
    210                 215                 220

Gly Leu Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Phe Thr Gly Asp Phe Asp Ser Val Ile Asp Cys Asn Thr Cys Val
            260                 265                 270

Thr Gln Thr Val Asp Phe Ser
            275

<210> SEQ ID NO 12
<211> LENGTH: 279
<212> TYPE: PRT
<213> ORGANISM: Hepatitis C virus

<400> SEQUENCE: 12

Met Gly Val Ala Lys Ala Val Asp Phe Ile Pro Val Glu Ser Met Glu
  1               5                  10                  15

Thr Thr Met Arg Ser Pro Val Phe Thr Asp Asn Ser Ser Pro Pro Ala
             20                  25                  30

Val Pro Gln Thr Phe Gln Val Ala His Leu His Ala Pro Thr Gly Ser
         35                  40                  45

Gly Lys Ser Thr Lys Val Pro Ala Ala Tyr Ala Ala Gln Gly Tyr Lys
     50                  55                  60

Val Leu Val Leu Asn Pro Ser Val Ala Ala Thr Leu Gly Phe Gly Ala
 65                  70                  75                  80

Tyr Met Ser Lys Ala His Gly Ile Asp Pro Gly Ile Arg Thr Gly Val
                 85                  90                  95

Arg Thr Ile Thr Thr Gly Ala Pro Ile Thr Tyr Ser Thr Tyr Gly Lys
            100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Ser Thr Thr Ile Leu Gly Ile Gly
        130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Asn Thr Gly Glu Ile Pro Phe Tyr Gly Lys
            180                 185                 190

Ala Ile Pro Leu Glu Thr Ile Lys Gly Gly Arg His Leu Ile Phe Cys
```

```
                195                 200                 205
His Ser Lys Lys Lys Cys Asp Glu Leu Ala Ala Lys Leu Ser Ser Leu
    210                 215                 220

Gly Leu Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Phe Thr Gly Asp Phe Asp Ser Val Ile Asp Cys Asn Thr Cys Val
                260                 265                 270

Thr Gln Thr Val Asp Phe Ser
        275

<210> SEQ ID NO 13
<211> LENGTH: 279
<212> TYPE: PRT
<213> ORGANISM: Hepatitis C virus

<400> SEQUENCE: 13

Met Gly Val Ala Lys Ala Val Asp Phe Ile Pro Val Glu Ser Met Glu
1               5                   10                  15

Thr Thr Met Arg Ser Pro Val Phe Thr Asp Asn Ser Ser Pro Pro Ala
                20                  25                  30

Val Pro Gln Thr Phe Gln Val Ala His Leu His Ala Pro Thr Gly Ser
            35                  40                  45

Gly Lys Ser Thr Lys Val Pro Ala Ala Tyr Ala Ala Gln Gly Tyr Lys
        50                  55                  60

Val Leu Val Leu Asn Pro Ser Val Ala Ala Thr Leu Gly Phe Gly Ala
65                  70                  75                  80

Tyr Met Ser Lys Ala His Gly Ile Asp Pro Gly Ile Arg Thr Gly Val
                85                  90                  95

Arg Thr Ile Thr Thr Gly Ala Pro Ile Thr Tyr Ser Thr Tyr Gly Lys
                100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Ser Thr Thr Ile Leu Gly Ile Gly
130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Asn Thr Gly Glu Ile Pro Phe Tyr Gly Lys
            180                 185                 190

Ala Ile Pro Leu Glu Thr Ile Lys Gly Gly Arg His Leu Ile Phe Cys
        195                 200                 205

His Ser Lys Lys Lys Cys Asp Glu Leu Ala Ala Lys Leu Ser Ser Leu
    210                 215                 220

Gly Leu Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Phe Thr Gly Asp Phe Asp Ser Val Ile Asp Cys Asn Thr Cys Val
                260                 265                 270

Thr Gln Thr Val Asp Phe Ser
        275
```

<210> SEQ ID NO 14
<211> LENGTH: 279
<212> TYPE: PRT
<213> ORGANISM: Hepatitis C virus

<400> SEQUENCE: 14

Met Gly Val Ala Lys Ala Val Asp Phe Ile Pro Val Glu Asn Leu Glu
1               5                   10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Gly Ser
        35                  40                  45

Gly Lys Ser Thr Lys Val Pro Ala Ala Tyr Ala Ala Gln Gly Tyr Lys
    50                  55                  60

Val Leu Val Leu Asn Pro Ser Val Ala Ala Thr Leu Gly Phe Gly Ala
65                  70                  75                  80

Tyr Met Ser Lys Ala His Gly Val Asp Pro Asn Ile Arg Thr Gly Val
                85                  90                  95

Arg Thr Ile Thr Thr Gly Ser Pro Ile Thr Tyr Ser Thr Tyr Gly Lys
            100                 105                 110

Phe Leu Ala Asp Gly Gly Cys Ser Gly Gly Ala Tyr Asp Ile Ile Ile
        115                 120                 125

Cys Asp Glu Cys His Ser Thr Asp Val Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Ile Phe Cys
        195                 200                 205

His Ser Lys Lys Lys Cys Asp Lys Leu Ala Ala Lys Leu Val Ala Leu
    210                 215                 220

Gly Ile Asn Ala Val Ala Tyr Tyr Arg Gly Leu Asp Val Ser Val Ile
225                 230                 235                 240

Pro Thr Ser Gly Asp Val Val Val Val Ala Thr Asp Ala Leu Met Thr
                245                 250                 255

Gly Tyr Thr Gly Asp Phe Asp Ser Val Ile Asp Cys Asn Thr Cys Val
            260                 265                 270

Thr Gln Thr Val Asp Ile Ser
        275

<210> SEQ ID NO 15
<211> LENGTH: 279
<212> TYPE: PRT
<213> ORGANISM: Hepatitis C virus

<400> SEQUENCE: 15

Met Gly Val Ala Lys Ala Val Asp Phe Ile Pro Val Glu Asn Leu Glu
1               5                   10                  15

Thr Thr Met Arg Ser Pro Val Phe Thr Asp Asn Ser Ser Pro Pro Ala
            20                  25                  30

Val Pro Gln Ser Phe Gln Val Ala His Leu His Ala Pro Thr Asp Ser
        35                  40                  45

Gly Lys Ser Thr Lys Val Pro Ala Ala Tyr Ala Ala Gln Gly Tyr Lys
    50                  55                  60

```
Val Leu Val Leu Asn Pro Ser Val Ala Ala Thr Leu Gly Phe Gly Ala
 65                  70                  75                  80

Tyr Met Ser Lys Ala His Gly Val Asp Pro Asn Ile Arg Thr Gly Val
                 85                  90                  95

Arg Thr Ile Thr Thr Gly Ser Pro Ile Thr Tyr Ser Thr Tyr Gly Lys
            100                 105                 110

Phe Leu Ala Asn Gly Gly Cys Ser Gly Gly Ala Tyr Asp Ile Ile Ile
            115                 120                 125

Cys Asp Glu Cys His Ser Thr Asp Val Thr Ser Ile Leu Gly Ile Gly
130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Ile Phe Cys
            195                 200                 205

His Ser Lys Lys Lys Cys Asp Glu Leu Ala Ala Lys Leu Val Ala Leu
210                 215                 220

Gly Ile Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
            245                 250                 255

Gly Tyr Thr Gly Asp Phe Asp Ser Val Ile Asp Cys Asn Thr Cys Val
            260                 265                 270

Thr Gln Thr Val Asp Phe Ser
            275

<210> SEQ ID NO 16
<211> LENGTH: 279
<212> TYPE: PRT
<213> ORGANISM: Hepatitis C virus

<400> SEQUENCE: 16

Met Gly Val Ala Lys Ala Val Asp Phe Ile Pro Val Glu Asn Leu Glu
  1               5                  10                  15

Thr Thr Met Arg Ser Pro Val Phe Thr Asp Asn Ser Ser Pro Pro Ala
                 20                  25                  30

Val Pro Gln Ser Phe Gln Val Ala His Leu His Ala Pro Thr Gly Ser
             35                  40                  45

Gly Lys Ser Thr Lys Val Pro Ala Ala Tyr Ala Ala Gln Gly Tyr Lys
         50                  55                  60

Val Leu Val Leu Asn Pro Ser Val Ala Ala Thr Leu Gly Phe Gly Ala
 65                  70                  75                  80

Tyr Met Ser Lys Ala His Gly Val Asp Pro Asn Ile Arg Thr Gly Val
                 85                  90                  95

Arg Thr Ile Thr Thr Gly Ser Pro Ile Thr Tyr Ser Thr Tyr Gly Lys
            100                 105                 110

Phe Leu Ala Asp Gly Gly Cys Ser Gly Gly Ala Tyr Asp Ile Ile Ile
            115                 120                 125

Cys Asp Glu Cys His Ser Thr Asp Val Thr Ser Ile Leu Gly Ile Gly
130                 135                 140

Thr Val Leu Asp Gln Ala Glu Thr Ala Gly Ala Arg Leu Val Val Leu
145                 150                 155                 160
```

```
Ala Thr Ala Thr Pro Pro Gly Ser Val Thr Val Pro His Pro Asn Ile
            165                 170                 175

Glu Glu Val Ala Leu Ser Thr Thr Gly Glu Ile Pro Phe Tyr Gly Lys
            180                 185                 190

Ala Ile Pro Leu Glu Ala Ile Lys Gly Gly Arg His Leu Ile Phe Cys
            195                 200                 205

His Ser Lys Lys Lys Cys Asp Glu Leu Ala Ala Lys Gln Val Ala Leu
        210                 215                 220

Gly Ile Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255

Gly Tyr Thr Gly Asp Phe Asp Ser Val Ile Asp Cys Asn Thr Cys Val
                260                 265                 270

Thr Gln Thr Val Asp Phe Ser
            275
```

<210> SEQ ID NO 17
<211> LENGTH: 279
<212> TYPE: PRT
<213> ORGANISM: Hepatitis C virus

<400> SEQUENCE: 17

```
Met Gly Val Ala Lys Ala Val Asp Phe Val Pro Val Glu Ser Met Glu
  1               5                  10                  15

Thr Thr Met Arg Ser Pro Val Phe Thr Asp Asn Ser Ser Pro Pro Ala
             20                  25                  30

Val Pro Gln Thr Phe Gln Val Ala His Leu His Ala Pro Thr Gly Ser
         35                  40                  45

Gly Lys Ser Thr Lys Val Pro Ala Ala Tyr Ala Ala Gln Gly Tyr Lys
     50                  55                  60

Val Leu Val Leu Asn Pro Ser Val Ala Ala Thr Leu Gly Phe Gly Ala
 65                  70                  75                  80

Tyr Met Ser Lys Ala His Gly Val Asp Pro Asn Ile Arg Thr Gly Val
                 85                  90                  95

Arg Thr Ile Thr Thr Gly Ala Pro Ile Thr Tyr Ser Thr Tyr Gly Lys
            100                 105                 110

Phe Leu Ala Asp Gly Gly Cys Ser Gly Gly Ala Tyr Asp Ile Ile Ile
        115                 120                 125

Cys Asp Glu Cys His Ser Ile Asp Ser Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
            165                 170                 175

Glu Glu Val Ala Leu Ser Ser Ile Gly Glu Ile Pro Phe Tyr Gly Lys
            180                 185                 190

Ala Ile Pro Ile Glu Val Ile Lys Gly Gly Arg His Leu Ile Phe Cys
            195                 200                 205

His Ser Lys Lys Lys Cys Asp Glu Leu Ala Ala Lys Leu Ser Gly Val
        210                 215                 220

Gly Ile Asn Ala Val Ala Tyr Tyr Arg Gly Leu Asp Val Ser Val Ile
225                 230                 235                 240

Pro Thr Ser Gly Asp Val Val Val Ala Thr Asp Ala Leu Met Thr
                245                 250                 255
```

```
Gly Phe Thr Gly Asp Phe Asp Ser Val Ile Asp Cys Asn Thr Cys Val
            260                 265                 270

Thr Gln Thr Val Asp Phe Ser
        275

<210> SEQ ID NO 18
<211> LENGTH: 279
<212> TYPE: PRT
<213> ORGANISM: Hepatitis C virus

<400> SEQUENCE: 18

Met Gly Val Ala Lys Ala Val Asp Phe Val Pro Val Glu Ser Met Glu
  1               5                  10                  15

Thr Thr Met Arg Ser Pro Val Phe Thr Asp Asn Ser Ser Pro Pro Ala
             20                  25                  30

Val Pro Gln Thr Phe Gln Val Ala His Leu His Ala Pro Thr Gly Ser
         35                  40                  45

Gly Lys Ser Thr Lys Val Pro Ala Ala Tyr Ala Ala Gln Gly Tyr Lys
     50                  55                  60

Val Leu Val Leu Asn Pro Ser Val Ala Ala Thr Leu Gly Phe Gly Ala
 65                  70                  75                  80

Tyr Met Ser Lys Ala His Gly Val Asp Pro Asn Ile Arg Thr Gly Val
                 85                  90                  95

Arg Thr Ile Thr Thr Gly Ala Pro Ile Thr Tyr Ser Thr Tyr Gly Lys
            100                 105                 110

Phe Leu Ala Asp Gly Gly Cys Ser Gly Gly Ala Tyr Asp Ile Ile Ile
        115                 120                 125

Cys Asp Glu Cys His Ser Ile Asp Ser Thr Ser Ile Leu Gly Ile Gly
    130                 135                 140

Thr Val Leu Asp Gln Ala Glu Thr Ala Gly Ala Arg Leu Val Val Leu
145                 150                 155                 160

Ala Thr Ala Thr Pro Pro Gly Ser Val Thr Val Pro His Pro Asn Ile
                165                 170                 175

Glu Glu Val Ala Leu Ser Ser Thr Gly Glu Ile Pro Phe Tyr Gly Lys
            180                 185                 190

Ala Ile Pro Ile Glu Val Ile Lys Gly Gly Arg His Leu Ile Phe Cys
        195                 200                 205

His Ser Lys Lys Lys Cys Asp Glu Leu Ala Ala Lys Leu Ser Gly Phe
    210                 215                 220

Gly Ile Asn Ala Val Ala Tyr Tyr Arg Gly Leu Asp Val Ser Val Ile
225                 230                 235                 240

Pro Thr Ser Gly Asp Val Val Val Val Ala Thr Asp Ala Leu Met Thr
                245                 250                 255

Gly Phe Thr Gly Asp Phe Asp Ser Val Ile Asp Cys Asn Thr Cys Val
            260                 265                 270

Thr Gln Thr Val Asp Phe Ser
        275

<210> SEQ ID NO 19
<211> LENGTH: 957
<212> TYPE: DNA
<213> ORGANISM: Hepatitis C virus

<400> SEQUENCE: 19
atggtaagat caagtagtca aaattcgagt gacaagcctg tagcccacgt cgtagcaaac      60
caccaagtgg aggagcaggg aattcaccat caccatcacc acgtggatcc cgggcccatg     120
```

```
ggggttgcga aggcggtgga ctttgtaccc gtagagtcta tggaaaccac catgcggtcc    180 ccggtctttta cggataactc atctcctccg gccgtaccgc agacattcca agtgcccat    240 ctacacgccc ccactggtag tggcaagagc actaaggtgc cggctgcata tgcagcccaa    300
gggtacaagg tacttgtcct gaacccatcc gttgccgcca ccttaggatt cggggcgtat    360
atgtctaaag cacatggtgt cgaccctaac attagaactg gggtaaggac catcaccacg    420 ggcgcccca ttacgtactc cacctacggc aagtttcttg ccgacggtgg ttgctctggg     480
ggcgcttacg acatcataat atgtgatgag tgccactcga ttgactcaac ctccatcttg    540
ggcatcggca ccgtcctgga tcaggcggag acggctggag cgcggcttgt cgtgctcgcc    600
actgctacac ctccggggtc ggtcaccgtg ccacatccca acatcgagga ggtggctctg    660
tccagcactg gagagatccc cttttatggc aaagccatcc ccatcgaggt catcaaaggg    720
gggaggcacc tcattttctg ccattccaag aagaaatgtg acgagctcgc cgcaaagcta    780
tcgggcttcg gaatcaacgc tgtagcgtat taccgaggcc ttgatgtgtc cgtcataccg    840
actagcggag acgtcgttgt tgtggcaaca gacgctctaa tgacgggctt accggcgac     900 tttgactcag tgatcgactg taacacatgc gtcacccaga cagtcgactt cagctaa      957

<210> SEQ ID NO 20
<211> LENGTH: 318
<212> TYPE: PRT
<213> ORGANISM: Hepatitis C virus

<400> SEQUENCE: 20

Met Val Arg Ser Ser Gln Asn Ser Ser Asp Lys Pro Val Ala His
 1               5                  10                  15

Val Val Ala Asn His Gln Val Glu Glu Gln Gly Ile His His His
            20                  25                  30

His His Val Asp Pro Gly Pro Met Gly Val Ala Lys Ala Val Asp Phe
        35                  40                  45

Val Pro Val Glu Ser Met Glu Thr Thr Met Arg Ser Pro Val Phe Thr
    50                  55                  60

Asp Asn Ser Ser Pro Pro Ala Val Pro Gln Thr Phe Gln Val Ala His
65                  70                  75                  80

Leu His Ala Pro Thr Gly Ser Gly Lys Ser Thr Lys Val Pro Ala Ala
                85                  90                  95

Tyr Ala Ala Gln Gly Tyr Lys Val Leu Val Leu Asn Pro Ser Val Ala
            100                 105                 110

Ala Thr Leu Gly Phe Gly Ala Tyr Met Ser Lys Ala His Gly Val Asp
        115                 120                 125

Pro Asn Ile Arg Thr Gly Val Arg Thr Ile Thr Gly Ala Pro Ile
    130                 135                 140

Thr Tyr Ser Thr Tyr Gly Lys Phe Leu Ala Asp Gly Gly Cys Ser Gly
145                 150                 155                 160

Gly Ala Tyr Asp Ile Ile Ile Cys Asp Glu Cys His Ser Ile Asp Ser
                165                 170                 175

Thr Ser Ile Leu Gly Ile Gly Thr Val Leu Asp Gln Ala Glu Thr Ala
            180                 185                 190

Gly Ala Arg Leu Val Val Leu Ala Thr Ala Thr Pro Pro Gly Ser Val
        195                 200                 205

Thr Val Pro His Pro Asn Ile Glu Glu Val Ala Leu Ser Ser Thr Gly
    210                 215                 220

Glu Ile Pro Phe Tyr Gly Lys Ala Ile Pro Ile Glu Val Ile Lys Gly
```

```
                225                 230                 235                 240
Gly Arg His Leu Ile Phe Cys His Ser Lys Lys Cys Asp Glu Leu
                    245                 250                 255

Ala Ala Lys Leu Ser Gly Phe Gly Ile Asn Ala Val Ala Tyr Tyr Arg
                260                 265                 270

Gly Leu Asp Val Ser Val Ile Pro Thr Ser Gly Asp Val Val Val
            275                 280                 285

Ala Thr Asp Ala Leu Met Thr Gly Phe Thr Gly Asp Phe Asp Ser Val
            290                 295                 300

Ile Asp Cys Asn Thr Cys Val Thr Gln Thr Val Asp Phe Ser
305                 310                 315

<210> SEQ ID NO 21
<211> LENGTH: 957
<212> TYPE: DNA
<213> ORGANISM: Hepatitis C virus

<400> SEQUENCE: 21
atggtaagat caagtagtca aaattcgagt gacaagcctg tagcccacgt cgtagcaaac      60
caccaagtgg aggagcaggg aattcaccat caccatcacc acgtggatcc cgggcccatg     120
ggggttgcga aggcggtgga ctttatcccc gtggagagcc tagaaacaac catgaggtcc     180
ccggtgttca cagacaactc ctccccgcca gcagtgcccc agagcttcca ggtggcccac     240
ctgcatgctc ccaccggcag cggtaagagc accaaggtcc cggccgcata tgcggctcag     300
ggctacaaag tgctggtgct caaccccctc cgttgctgca cattgggctt tggtgcttac     360
atgtccaagg cccatgggat tgatcctaac atcaggactg ggtaaggac aattactact     420 ggcagcccca tcacgtactc cacctacggc aagttccttg ccgacggcgg gtgctcgggg     480
ggtgcttatg acataataat ttgtgacgag tgccactcca cagatgcaac atctattttg     540
ggcatcggca ctgtccttga ccaagcagag actgcggggg cgagactggt tgtgcttgcc     600
accgctaccc ctccgggctc cgtcactgtg ccccatccta atatcgagga ggttgctctg     660
tccaccaccg gagagatccc cttttacggc aaggctatcc cccttgaggc aatcaaaggg     720
gggagacatc tcatcttctg ccactcaaag aagaagtgcg acgaactcgc cgccaaaccg     780
gtcgcgttgg gtgtcaatgc cgtggcttac taccgcggcc ttgacgtgcc cgtcatcccg     840
accagtggcg atgttgtcgt cgtggcaact gatgctctca tgaccggttt taccggtgac     900
ttcgactcgg tgatagactg taatacgtgt gtcacccaga cagtcgactt cagctaa       957

<210> SEQ ID NO 22
<211> LENGTH: 318
<212> TYPE: PRT
<213> ORGANISM: Hepatitis C virus

<400> SEQUENCE: 22

Met Val Arg Ser Ser Gln Asn Ser Ser Asp Lys Pro Val Ala His
  1               5                  10                  15

Val Val Ala Asn His Gln Val Glu Glu Gln Gly Ile His His His
                20                  25                  30

His His Val Asp Pro Gly Pro Met Gly Val Ala Lys Ala Val Asp Phe
            35                  40                  45

Ile Pro Val Glu Ser Leu Glu Thr Thr Met Arg Ser Pro Val Phe Thr
    50                  55                  60

Asp Asn Ser Ser Pro Pro Ala Val Pro Gln Ser Phe Gln Val Ala His
65                  70                  75                  80
```

Leu His Ala Pro Thr Gly Ser Gly Lys Ser Thr Lys Val Pro Ala Ala
            85                  90                  95

Tyr Ala Ala Gln Gly Tyr Lys Val Leu Val Leu Asn Pro Ser Val Ala
        100                 105                 110

Ala Thr Leu Gly Phe Gly Ala Tyr Met Ser Lys Ala His Gly Ile Asp
    115                 120                 125

Pro Asn Ile Arg Thr Gly Val Arg Thr Ile Thr Thr Gly Ser Pro Ile
130                 135                 140

Thr Tyr Ser Thr Tyr Gly Lys Phe Leu Ala Asp Gly Gly Cys Ser Gly
145                 150                 155                 160

Gly Ala Tyr Asp Ile Ile Cys Asp Glu Cys His Ser Thr Asp Ala
                165                 170                 175

Thr Ser Ile Leu Gly Ile Gly Thr Val Leu Asp Gln Ala Glu Thr Ala
            180                 185                 190

Gly Ala Arg Leu Val Val Leu Ala Thr Ala Thr Pro Pro Gly Ser Val
        195                 200                 205

Thr Val Pro His Pro Asn Ile Glu Glu Val Ala Leu Ser Thr Thr Gly
    210                 215                 220

Glu Ile Pro Phe Tyr Gly Lys Ala Ile Pro Leu Glu Ala Ile Lys Gly
225                 230                 235                 240

Gly Arg His Leu Ile Phe Cys His Ser Lys Lys Lys Cys Asp Glu Leu
                245                 250                 255

Ala Ala Lys Pro Val Ala Leu Gly Val Asn Ala Val Ala Tyr Tyr Arg
            260                 265                 270

Gly Leu Asp Val Pro Val Ile Pro Thr Ser Gly Asp Val Val Val Val
        275                 280                 285

Ala Thr Asp Ala Leu Met Thr Gly Phe Thr Gly Asp Phe Asp Ser Val
    290                 295                 300

Ile Asp Cys Asn Thr Cys Val Thr Gln Thr Val Asp Phe Ser
305                 310                 315

<210> SEQ ID NO 23
<211> LENGTH: 981
<212> TYPE: DNA
<213> ORGANISM: Hepatitis C virus

<400> SEQUENCE: 23
atggtaagat caagtagtca aaattcgagt gacaagcctg tagcccacgt cgtagcaaac      60
caccaagtgg aggagcaggg aattcaccat caccatcacc acgtggatcc cgggcccatg     120
gccgcgggat tgggcccccc cataggtgta gcaaaagccc tacagttcat accagtggaa     180
acccttagta cgcaggctag gtctccatct ttctctgaca attcaactcc tcctgctgtc     240
ccacagagct atcaagtagg gtatcttcat gccccgaccg gcagcggtaa gagcacaaag     300
gtcccggccg cttatgtagc acaaggatat aatgttctcg tgctgaatcc atcggtggcg     360
gccacactag gcttcggctc tttcatgtcg cgtgcctatg gatcgaccc caacatccgc      420 actgggaacc gcaccgtcac aactggtgct aaactgacct attccaccta cggtaagttt     480
ctcgcggacg ggggttgctc cggggggca tatgatgtaa ttatctgtga tgaatgtcat     540
gcccaagacg ccactagcat attgggcata ggcacggtct tagatcaggc cgagacggct     600
ggggtgaggc tgacggtttt agcgacagca actcccccag gcagcatcac tgtgccacat     660
tctaacatcg aggaagtggc cctgggctct gaaggtgaga tcccttttcta cggtaaggct     720 ataccgatag ccctgctcaa gggggggaga cacctcgtct tttgccattc caagaaaaaa     780
tgtgatgagc tagcatccaa actcagaggt atggggctca acgctgtggc gtactatagg     840

-continued

```
ggtctcgatg tttccgtcat accaacaaca ggagacgtcg tggtctgcgc tactgacgcc    900
ctcatgactg gattcactgg agacttcgat tctgtcatag actgcaacgt ggctgttgaa    960
cagtacgttg acttcagcta a                                              981
```

<210> SEQ ID NO 24
<211> LENGTH: 326
<212> TYPE: PRT
<213> ORGANISM: Hepatitis C virus

<400> SEQUENCE: 24

```
Met Val Arg Ser Ser Gln Asn Ser Ser Asp Lys Pro Val Ala His
 1               5                   10                  15

Val Val Ala Asn His Gln Val Glu Glu Gln Gly Ile His His His
                20                  25                  30

His His Val Asp Pro Gly Pro Met Ala Ala Gly Leu Gly Pro Ile
                35                  40                  45

Gly Val Ala Lys Ala Leu Gln Phe Ile Pro Val Glu Thr Leu Ser Thr
 50                  55                  60

Gln Ala Arg Ser Pro Ser Phe Ser Asp Asn Ser Thr Pro Pro Ala Val
 65                  70                  75                  80

Pro Gln Ser Tyr Gln Val Gly Tyr Leu His Ala Pro Thr Gly Ser Gly
                 85                  90                  95

Lys Ser Thr Lys Val Pro Ala Ala Tyr Val Ala Gln Gly Tyr Asn Val
                100                 105                 110

Leu Val Leu Asn Pro Ser Val Ala Ala Thr Leu Gly Phe Gly Ser Phe
                115                 120                 125

Met Ser Arg Ala Tyr Gly Ile Asp Pro Asn Ile Arg Thr Gly Asn Arg
130                 135                 140

Thr Val Thr Thr Gly Ala Lys Leu Thr Tyr Ser Thr Tyr Gly Lys Phe
145                 150                 155                 160

Leu Ala Asp Gly Gly Cys Ser Gly Gly Ala Tyr Asp Val Ile Ile Cys
                165                 170                 175

Asp Glu Cys His Ala Gln Asp Ala Thr Ser Ile Leu Gly Ile Gly Thr
                180                 185                 190

Val Leu Asp Gln Ala Glu Thr Ala Gly Val Arg Leu Thr Val Leu Ala
                195                 200                 205

Thr Ala Thr Pro Pro Gly Ser Ile Thr Val Pro His Ser Asn Ile Glu
210                 215                 220

Glu Val Ala Leu Gly Ser Gly Gly Ile Pro Phe Tyr Gly Lys Ala
225                 230                 235                 240

Ile Pro Ile Ala Leu Leu Lys Gly Gly Arg His Leu Val Phe Cys His
                245                 250                 255

Ser Lys Lys Lys Cys Asp Glu Leu Ala Ser Lys Leu Arg Gly Met Gly
                260                 265                 270

Leu Asn Ala Val Ala Tyr Tyr Arg Gly Leu Asp Val Ser Val Ile Pro
                275                 280                 285

Thr Thr Gly Asp Val Val Cys Ala Thr Asp Ala Leu Met Thr Gly
                290                 295                 300

Phe Thr Gly Asp Phe Asp Ser Val Ile Asp Cys Asn Val Ala Val Glu
305                 310                 315                 320

Gln Tyr Val Asp Phe Ser
                325
```

<210> SEQ ID NO 25

-continued

```
<211> LENGTH: 981
<212> TYPE: DNA
<213> ORGANISM: Hepatitis C virus

<400> SEQUENCE: 25
atggtaagat caagtagtca aaattcgagt gacaagcctg tagcccacgt cgtagcaaac      60 cacca

Asp Glu Cys His Ala Gln Asp Ala Thr Ser Ile Leu Gly Ile Gly Thr
            180                 185                 190

Val Leu Asp Gln Ala Glu Thr Ala Gly Val Arg Leu Thr Val Leu Ala
        195                 200                 205

Thr Ala Thr Pro Pro Gly Ser Ile Thr Val Pro His Ser Asn Ile Glu
    210                 215                 220

Glu Val Ala Leu Gly Ser Glu Gly Glu Ile Pro Phe Tyr Gly Lys Ala
225                 230                 235                 240

Ile Pro Ile Ser Leu Leu Lys Gly Gly Arg His Leu Ile Phe Cys His
                245                 250                 255

Ser Lys Lys Lys Cys Asp Lys Ile Ala Ser Lys Leu Arg Gly Met Gly
            260                 265                 270

Leu Asn Ala Val Ala Tyr Tyr Arg Gly Leu Asp Val Ser Val Ile Pro
        275                 280                 285

Thr Thr Gly Asp Val Val Cys Ala Thr Asp Ala Leu Met Thr Gly
    290                 295                 300

Tyr Thr Gly Asp Phe Asp Ser Val Ile Asp Cys Asn Val Ala Val Glu
305                 310                 315                 320

Gln Tyr Val Asp Phe Ser
            325

<210> SEQ ID NO 27
<211> LENGTH: 957
<212> TYPE: DNA
<213> ORGANISM: Hepatitis C virus

<400> SEQUENCE: 27
atggtaagat caagtagtca aaattcgagt gacaagcctg tagcccacgt cgtagcaaac      60
caccaagtgg aggagcaggg aattcaccat caccatcacc acgtggatcc cgggcccatg     120
ggcgtggcca gtccataga cttcatcccc gttgagacac tcgacatcgt acgcggtcc      180
cccaccttta gtgacaacag cacgccaccg gctgtgcccc agacctatca ggtcgggtac     240
tgcatgccc caaccggcag cggaaagagc accaaagtcc ccgtcgcata cgccgcccag     300
gggtataaag tgttagtgct caatcccctcg gtggctgcta ccctggggtt tggagcgtac     360
ctgtccaagg cacacggcat caatcccaac attaggactg gagtcaggac tgtgacgact     420
ggcgaagcca tcacgtactc cacgtatggc aaattcctcg ccgatggggg ctgcgcaggt     480
ggcgcctatg acatcatcat atgcgatgaa tgccacgccg tggatgccac taccattctc     540
ggcatcggaa cagtccttga ccaagcagag acagccgggg tcaggctaac tgtgctggct     600
acggccacgc cccccgggtc agtgacaacc cccatccca acatagagga ggtagccctc     660
gggcaggagg gtgagacccc cttctatggg agggcgatcc ccctgtctta catcaaggga     720
gggagacact tgatcttctg ccactcaaag aaaaagtgtg acgagctcgc ggcggccctc     780
cggggcatgg gcctgaacgc tgtggcgtac tacagagggc tcgacgtctc cgtaatacca     840
gctcagggag atgtagtggt cgtcgccacc gacgccctca tgacggggtt cactggagac     900
tttgactccg tgatcgactg caatgtagcg gtcactcaag ttgtagactt cagctaa       957

<210> SEQ ID NO 28
<211> LENGTH: 318
<212> TYPE: PRT
<213> ORGANISM: Hepatitis C virus

<400> SEQUENCE: 28

Met Val Arg Ser Ser Ser Gln Asn Ser Ser Asp Lys Pro Val Ala His

```
                1               5                  10                 15
              Val Val Ala Asn His Gln Val Glu Glu Gln Gly Ile His His His
                             20                  25                  30

His His Val Asp Pro Gly Pro Met Gly Val Ala Lys Ser Ile Asp Phe
                             35                  40                  45

Ile Pro Val Glu Thr Leu Asp Ile Val Thr Arg Ser Pro Thr Phe Ser
               50                  55                  60

Asp Asn Ser Thr Pro Pro Ala Val Pro Gln Thr Tyr Gln Val Gly Tyr
               65                  70                  75                  80

Leu His Ala Pro Thr Gly Ser Gly Lys Ser Thr Lys Val Pro Val Ala
                                 85                  90                  95

Tyr Ala Ala Gln Gly Tyr Lys Val Leu Val Leu Asn Pro Ser Val Ala
                                100                 105                 110

Ala Thr Leu Gly Phe Gly Ala Tyr Leu Ser Lys Ala His Gly Ile Asn
                                115                 120                 125

Pro Asn Ile Arg Thr Gly Val Arg Thr Val Thr Thr Gly Glu Ala Ile
                            130                 135                 140

Thr Tyr Ser Thr Tyr Gly Lys Phe Leu Ala Asp Gly Gly Cys Ala Gly
              145                 150                 155                 160

Gly Ala Tyr Asp Ile Ile Ile Cys Asp Glu Cys His Ala Val Asp Ala
                                165                 170                 175

Thr Thr Ile Leu Gly Ile Gly Thr Val Leu Asp Gln Ala Glu Thr Ala
                            180                 185                 190

Gly Val Arg Leu Thr Val Leu Ala Thr Ala Thr Pro Pro Gly Ser Val
                            195                 200                 205

Thr Thr Pro His Pro Asn Ile Glu Glu Val Ala Leu Gly Gln Glu Gly
                            210                 215                 220

Glu Thr Pro Phe Tyr Gly Arg Ala Ile Pro Leu Ser Tyr Ile Lys Gly
              225                 230                 235                 240

Gly Arg His Leu Ile Phe Cys His Ser Lys Lys Lys Cys Asp Glu Leu
                                245                 250                 255

Ala Ala Ala Leu Arg Gly Met Gly Leu Asn Ala Val Ala Tyr Tyr Arg
                            260                 265                 270

Gly Leu Asp Val Ser Val Ile Pro Ala Gln Gly Asp Val Val Val Val
                            275                 280                 285

Ala Thr Asp Ala Leu Met Thr Gly Phe Thr Gly Asp Phe Asp Ser Val
                            290                 295                 300

Ile Asp Cys Asn Val Ala Val Thr Gln Val Val Asp Phe Ser
              305                 310                 315

<210> SEQ ID NO 29
<211> LENGTH: 957
<212> TYPE: DNA
<213> ORGANISM: Hepatitis C virus

<400> SEQUENCE: 29
atggtaagat caagtagtca aaattcgagt gacaagcctg tagcccacgt cgtagcaaac    60
caccaagtgg aggagcaggg aattcaccat caccatcacc acgtggatcc cgggcccatg   120
ggcgtagcca aatccattga cttcatccct gttgaatctc tcgatatcgc ctcacggtca   180 cccagttttct ctgacaacag cacgccacca gctgtgcctc agtcctacca ggtgggctat   240
ttgcacgcgc aacgggcag cgggaagagc accaaggtcc ctgtcgcata tgctagtcag   300
gggtataaag tactcgtgct aaatccctct gtcgcggcca cgtcggctt cggggcctac   360 atgtccaaag cccacgggat caaccccaac atcagaaccg ggtacggac tgtgaccacc   420
```

```
gggacccca tcacctactc cacttatggc aagtttctcg cagatggggg ctgctcagcc    480
ggcgcctatg atgtcatcat atgcgatgaa tgccactcag tggacgctac taccatcctt    540
ggcattggaa cagtcctcga ccaggccgag accgcgggtg ctaggttagt ggttttagcc    600
acagccacgc ctcctggtac agtgacaact cctcatagca catagagga ggtggctctt    660 ggtcatgaag gcgagatccc tttctacggc aaggctattc ccctagcttt catcaagggg    720
ggcagacacc taatctttg ccattcaaag aagaagtgcg atgagctcgc ggcagccctt    780
cggggcatgg gtgtcaacgc cgttgcttac tatggggtc tcgacgtctc tgttatacca    840
actcaaggag acgtggtggt cgttgccacc gatgccctaa tgactggata caccggtgac    900
tttgactctg ttattgactg caacgttgcg gtctctcaaa ttgtagactt cagctaa    957
```

<210> SEQ ID NO 30
<211> LENGTH: 318
<212> TYPE: PRT
<213> ORGANISM: Hepatitis C virus

<400> SEQUENCE: 30

```
Met Val Arg Ser Ser Gln Asn Ser Ser Asp Lys Pro Val Ala His
  1               5                  10                  15

Val Val Ala Asn His Gln Val Glu Glu Gln Gly Ile His His His
                 20                  25                  30

His His Val Asp Pro Gly Pro Met Gly Val Ala Lys Ser Ile Asp Phe
             35                  40                  45

Ile Pro Val Glu Ser Leu Asp Ile Ala Ser Arg Ser Pro Ser Phe Ser
         50                  55                  60

Asp Asn Ser Thr Pro Pro Ala Val Pro Gln Ser Tyr Gln Val Gly Tyr
 65                  70                  75                  80

Leu His Ala Pro Thr Gly Ser Gly Lys Ser Thr Lys Val Pro Val Ala
                 85                  90                  95

Tyr Ala Ser Gln Gly Tyr Lys Val Leu Val Leu Asn Pro Ser Val Ala
                100                 105                 110

Ala Thr Leu Gly Phe Gly Ala Tyr Met Ser Lys Ala His Gly Ile Asn
            115                 120                 125

Pro Asn Ile Arg Thr Gly Val Arg Thr Val Thr Thr Gly Asp Pro Ile
        130                 135                 140

Thr Tyr Ser Thr Tyr Gly Lys Phe Leu Ala Asp Gly Gly Cys Ser Ala
145                 150                 155                 160

Gly Ala Tyr Asp Val Ile Ile Cys Asp Glu Cys His Ser Val Asp Ala
                165                 170                 175

Thr Thr Ile Leu Gly Ile Gly Thr Val Leu Asp Gln Ala Glu Thr Ala
            180                 185                 190

Gly Ala Arg Leu Val Val Leu Ala Thr Ala Thr Pro Pro Gly Thr Val
        195                 200                 205

Thr Thr Pro His Ser Asn Ile Glu Glu Val Ala Leu Gly His Glu Gly
    210                 215                 220

Glu Ile Pro Phe Tyr Gly Lys Ala Ile Pro Leu Ala Phe Ile Lys Gly
225                 230                 235                 240

Gly Arg His Leu Ile Phe Cys His Ser Lys Lys Lys Cys Asp Glu Leu
                245                 250                 255

Ala Ala Ala Leu Arg Gly Met Gly Val Asn Ala Val Ala Tyr Tyr Arg
            260                 265                 270

Gly Leu Asp Val Ser Val Ile Pro Thr Gln Gly Asp Val Val Val Val
        275                 280                 285
```

Ala Thr Asp Ala Leu Met Thr Gly Tyr Thr Gly Asp Phe Asp Ser Val
    290                 295                 300

Ile Asp Cys Asn Val Ala Val Ser Gln Ile Val Asp Phe Ser
305                 310                 315

<210> SEQ ID NO 31
<211> LENGTH: 957
<212> TYPE: DNA
<213> ORGANISM: Hepatitis C virus

<400> SEQUENCE: 31
atggtaagat caagtagtca aaattcgagt gacaagcctg tagcccacgt cgtagcaaac      60
caccaagtgg aggagcaggg aattcaccat caccatcacc acgtggatcc cgggcccatg     120
ggcgtagcca aatccattga cttcatcccc gttgagtctc tcgacatcgt gactaggtct     180
ccaagcttca ctgacaacag tacacctcca gccgtgcctc agacctacca agtgggtat      240 ctccacgcgc ccactggtag cgggaagagt accaaggtcc tgcagcgta cgccgctcag     300 gggtacaagg tgctggtact gaaccccctcc gtggctgcca ctttgggatt tggggcctac     360
atgtcaaaag cgcacggagt caatcccaat atcaggaccg gggttcgcac ggtgaacact     420
ggggatccca tcacctactc cacgtatggc aaattcctcg cagatggagg ctgctctgga     480
ggcgcctatg gcatcataat atgcgacgaa tgccattcga cggactccac gaccatcctc     540
ggcatcggga ccgttctcga ccaagctgag acagctggag ttaggttggt ggtcttggcc     600
acggcgaccc cacccggatc tgtaacaacc ccacacccca acatagagga ggtggccctc     660
ggccacgagg gcgaaatccc cttctatggg aaggccatcc ctctctcaac catcaaggga     720
ggacgacatc taatcttctg tcattcaaag aaaaagtgcg acgagctcgc ggtggccctc     780
cgagcgatgg gccttaacgc ggtggcatac tacagagggc ttgacgtctc cgtgataccg     840
acacaaggag acgtggtggt cgtcgccacc gacgccctca tgacaggata tactggagac     900
ttcgactctg tgatcgactg caacatggcg gtctctcaaa ttgtagactt cagctaa       957

<210> SEQ ID NO 32
<211> LENGTH: 318
<212> TYPE: PRT
<213> ORGANISM: Hepatitis C virus

<400> SEQUENCE: 32

Met Val Arg Ser Ser Gln Asn Ser Ser Asp Lys Pro Val Ala His
  1               5                  10                  15

Val Val Ala Asn His Gln Val Glu Glu Gln Gly Ile His His His
                 20                  25                  30

His His Val Asp Pro Gly Pro Met Gly Val Ala Lys Ser Ile Asp Phe
             35                  40                  45

Ile Pro Val Glu Ser Leu Asp Ile Val Thr Arg Ser Pro Ser Phe Thr
     50                  55                  60

Asp Asn Ser Thr Pro Pro Ala Val Pro Gln Thr Tyr Gln Val Gly Tyr
 65                  70                  75                  80

Leu His Ala Pro Thr Gly Ser Gly Lys Ser Thr Lys Val Pro Ala Ala
                 85                  90                  95

Tyr Ala Ala Gln Gly Tyr Lys Val Leu Val Leu Asn Pro Ser Val Ala
                100                 105                 110

Ala Thr Leu Gly Phe Gly Ala Tyr Met Ser Lys Ala His Gly Val Asn
            115                 120                 125

Pro Asn Ile Arg Thr Gly Val Arg Thr Val Asn Thr Gly Asp Pro Ile

```
                130                 135                 140
Thr Tyr Ser Thr Tyr Gly Lys Phe Leu Ala Asp Gly Gly Cys Ser Gly
145                 150                 155                 160

Gly Ala Tyr Gly Ile Ile Ile Cys Asp Glu Cys His Ser Thr Asp Ser
                165                 170                 175

Thr Thr Ile Leu Gly Ile Gly Thr Val Leu Asp Gln Ala Glu Thr Ala
            180                 185                 190

Gly Val Arg Leu Val Val Leu Ala Thr Ala Thr Pro Pro Gly Ser Val
        195                 200                 205

Thr Thr Pro His Pro Asn Ile Glu Glu Val Ala Leu Gly His Glu Gly
    210                 215                 220

Glu Ile Pro Phe Tyr Gly Lys Ala Ile Pro Leu Ser Thr Ile Lys Gly
225                 230                 235                 240

Gly Arg His Leu Ile Phe Cys His Ser Lys Lys Cys Asp Glu Leu
                245                 250                 255

Ala Val Ala Leu Arg Ala Met Gly Leu Asn Ala Val Ala Tyr Tyr Arg
            260                 265                 270

Gly Leu Asp Val Ser Val Ile Pro Thr Gln Gly Asp Val Val Val Val
        275                 280                 285

Ala Thr Asp Ala Leu Met Thr Gly Tyr Thr Gly Asp Phe Asp Ser Val
    290                 295                 300

Ile Asp Cys Asn Met Ala Val Ser Gln Ile Val Asp Phe Ser
305                 310                 315
```

<210> SEQ ID NO 33
<211> LENGTH: 36
<212> TYPE: DNA
<213> ORGANISM: Hepatitis C virus

<400> SEQUENCE: 33
gggccccacc ataggtgtag caaaagccct acagtt                         36

<210> SEQ ID NO 34
<211> LENGTH: 33
<212> TYPE: DNA
<213> ORGANISM: Hepatitis C virus

<400> SEQUENCE: 34
ctattagctg aagtcaacgt actgttcaac agc                            33

<210> SEQ ID NO 35
<211> LENGTH: 36
<212> TYPE: DNA
<213> ORGANISM: Hepatitis C virus

<400> SEQUENCE: 35
gggccccacc atgggcgtgg ccaagtccat agactt                         36

<210> SEQ ID NO 36
<211> LENGTH: 33
<212> TYPE: DNA
<213> ORGANISM: Hepatitis C virus

<400> SEQUENCE: 36
ctattagctg aagtctacaa cttgagtgac cgc                            33

<210> SEQ ID NO 37
<211> LENGTH: 36
<212> TYPE: DNA
<213> ORGANISM: Hepatitis C virus

```
<400> SEQUENCE: 37
gggccccacc atgggcgtag ccaaatccat tgactt                          36

<210> SEQ ID NO 38
<211> LENGTH: 33
<212> TYPE: DNA
<213> ORGANISM: Hepatitis C virus

<400> SEQUENCE: 38
ctattagctg aagtctacaa tttgagagac cgc                             33
```

IMMUNODIAGNOSTIC ASSAYS USING REDUCING AGENTS

The present application is a divisional of U.S. application Ser. No. 09/686,964, filed Oct. 12, 2000 (abandoned), which is a continuation of PCT/EP99/02547, filed Apr. 15, 1999, which claims benefit of EP 98870087.8, filed Apr. 17, 1998, the entire contents of each of which is hereby incorporated by reference in this application.

FIELD OF THE INVENTION

The present invention relates to the field of diagnosis and treatment of HCV infection. More particularly, the present invention relates to HCV NS3 helicase and its uses. Also the present invention relates to improved immunodiagnostic assays.

BACKGROUND OF THE INVENTION

Hepatitis C Viruses (HCV) constitute a senus within the Flaviviridae, with closest homology to the hepatitis G and GB viruses, and Pestiviruses. The positive-stranded RNA genome encodes at least 9 proteins. Core, E1, and E2 constitute the structural proteins. NS2, NS3, NS4A, NS4B, NS5A, and NS5B are non-structural (NS) proteins. HCV isolates display high levels of sequence heterogeneity allowing classification into at least 11 types and 90 subtypes (Maertens and Stuyver, 1997). HCV infection of the human liver is often clinically benign, with mild icterus in the acute phase. The disease may even go unnoticed in some cases of acute resolving hepatitis C. In the majority (>70%) of cases, however, HCV infection leads to chronic persistent or active infection, often with complications of liver cirrhosis and auto-immune disorders. Hepatocellular carcinoma may occur after about 20 to 35 years (Saito et al., 1990), sometimes even without the intermediate phase of cirrhosis. No prophylaxis is available today and treatment with interferon-alpha (IFN-α) only leads to long-term resolution in about 4 to 36% of treated cases, depending on the HCV genotype (Maertens and Stuyver, 1997).

Since productive culture methods for HCV are currently not available, and since only minute amounts of HCV antigens circulate in the infected patient, direct detection of HCV particles cannot be performed routinely, and indirect diagnosis is only possible using cumbersome amplification techniques for HCV RNA detection. Unlike with many other viral infections, HCV particles generally persist in the blood, liver, and lymphocytes despite the presence of cellular and humoral immune response to most of the HCV proteins. HCV antibodies can be conveniently detected by Elisa techniques which allow high throughput screening in blood banks and clinical laboratories. Supplementary antibody testing is required and is now mandatory in most countries. True HCV reactivity is thus discriminated from false reactivity, which may be caused by non-specific binding of serum or plasma immunoglobulines or anti-idiotypic components to the coating or blocking reagents, or to contaminants present in HCV antigen preparations, or even to fusion parts or non-specific regions of the recombinant antigens themselves (McFarlane et al., 1990). HCV RNA detection by PCR or branched DNA (bDNA) techniques have recently been introduced to monitor chronic HCV disease, especially during therapy. Surprisingly, HCV RNA detection is sometimes employed to confirm HCV Ab screening tests, despite the fact that only ~70-94% of repeatedly HCV Ab positive patient samples are positive by nested PCR (Marin et al., 1994). Of HCV Ab positive blood donors, who usually present with milder forms of the disease and low HCV RNA levels, confirmation by nested PCR is usually in the order of ~40% (Waumans et al., 1993; Stuyver et al., 1996). Strip-based assays therefore provide the only reliable alternative for HCV Ab confirmation. Even in the case of an indeterminate result in the confirmatory assay, serological follow up of the patient rather than HCV RNA detection is advisable (Di Biscealie et al., 1998). Since native HCV antigens are not available insufficient quantities, such confirmatory assays incorporate synthetic peptides and/or recombinant fragments of HCV proteins. One of the most critical issues in the confirmation of antibodies constitutes the reactivity of the NS3 protein (Zaaijer et al., 1994). NS3 antibodies often appear first in seroconversion series and the reactivity of the NS3 protein seems to be different in the different commercial assays available today.

Innogenetics introduced the concept of strip technology in which usually a combination of synthetic peptides and recombinant proteins are applied as discrete lines in an ordered and easily readable fashion. The INNO-LIA HIV Ab tests have proven to be superior to routinely used western blots (Pollet et al., 1990). The Line Immuno Assay allows multiparameter testing and thus enables incorporation of cut-off and other rating systems, sample addition control, as well as testing for false reactivity to non-HCV proteins used as carrier or fusion partner required for some antigens in the Elisa test. In principle, the test format allows to combine antigens of different aetiological agents or phenotypically linked conditions into a single test.

The INNO-LIA HCV Ab III is a 3rd generation Line Immuno Assay which incorporates HCV antigens derived from the Core region, the E2 hypervariable region (HVR), the NS3 helicase region, and the NS4A, NS4B, and NS5A regions. In the third generation assay, highly purified recombinant subtype 1b NS3 protein and E2 peptides enabled superior sensitivity while safeguarding the reliable specificity which is characteristic of peptide-based tests (Peeters et al., 1993). Perhaps one of the most important features of this assay is its unprecedented correlation with HCV RNA positivity (Claeys et al., 1992; De Beenhouwer et al., 1992).

The antigens are coated as 6 discrete lines on a nylon strip with plastic backing. In addition, four control lines are coated on each strip: anti-streptavidin, 3+positive control (anti-human Ig), 1+ positive control (human IgG), and the ± cutoff line (human IgG). A diluted test sample is incubated in a trough together with the LIA III strip. If present in the sample, HCV antibodies will bind to the HCV antigen lines on the strip. Subsequently, an affinity-purified alkaline phosphatase labelled goat anti-human IgG (H+L) conjugate is added and reacts with specific HCV antigen/antibody complexes if previously formed. Incubation with enzyme substrate produces a chestnut-like color, the intensity of which is proportionate to the amount of HCV-specific antibody captured from the sample on any given line. Color development is stopped with sulphuric acid. If no HCV-specific antibodies are present, the conjugate only binds to the ±, 1+, and 3+ control lines. If the addition of sample is omitted, only the ± and 1+ control lines will be stained.

DEFINITIONS

The following definitions serve to illustrate the different terms and expressions used in the present invention.

The term 'HCV NS3' protein refers to a polypeptide or an analogue thereof (e.g. mimotopes) comprising an amino acid sequence (and/or amino acid analogues) defining at least one HCV epitope of either HCV NS3 protease or helicase.

The term 'hepatitis C virus envelope protein' refers to a polypeptide or an analogue thereof (e.g. mimotopes) comprising an amino acid sequence (and/or amino acid analogues) defining at least one HCV epitope of either the E1 or the E2 region (see WO 96/04385 of which the contents are hereby incorporated by reference).

It should also be understood that the isolates (biological samples) used in the examples section of the present invention were not intended to limit the scope of the invention and that any HCV isolate belonging to type 1, 2, 3, 4, 5, 6, 7, 8, 9, 10, 11, 12 or any other new genotype of HCV is a suitable source of HCV sequence for the practice of the present invention.

The HCV antigens used in the present invention may be full-length viral proteins, substantially full-length versions thereof, or functional fragments thereof (e.g. fragments which are not missing sequence essential to the formation or retention of an epitope). Furthermore, the HCV antigens of the present invention can also include other sequences that do not block or prevent the formation of any conformational epitope of interest. The presence or absence of a conformational epitope can be readily determined though screening the antigen of interest with an antibody (polyclonal serum or monoclonal antibody) and comparing its reactivity to that of a denatured version of the antigen which retains only linear epitopes (if any). When in such screening polyclonal antibodies are used, it may be advantageous to adsorb the polyclonal serum first with the denatured antigen and see if it retains antibodies to the antigen of interest.

The term 'fusion polypeptide' intends a polypeptide in which the antigen(s), in particularly HCV antigen(s), are part of a single continuous chain of amino acids, which chain does not occur in nature. The HCV antigens may be connected directly to each other by peptide bonds or be separated by spacer amino acid sequences. The fusion polypeptides may also contain amino acid sequences exogenous to HCV.

The term 'solid phase' or 'solid support' means a solid body to which the individual HCV antigens or the fusion polypeptide comprised of HCV antigens are bound covalently or by noncovalent means such as by hydrophobic adsorption. Examples of solid phases are microtiter plates, membrane strips such as nylon or nitrocellulose strips, and silicon chips.

The term 'biological sample' intends a fluid or tissue of a mammalian individual (e.g. an anthropoid, a human) that commonly contains antibodies produced by the individual, more particularly antibodies against HCV. The fluid or tissue may also contain HCV antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological liquid' refers to a fluid obtained from an organism. Some biological fluids are used as a source of other products, such as clotting factors (e.g. Factor VIII), serum albumin, growth hormone and the like. In such cases, it is important -that the source of biological fluid be free of contamination by virus such as HCV.

The term 'immunologically reactive' means that the antigen in question will react specifically with anti-HCV antibodies present in a body component from an HCV infected individual or an immunized individual.

The term 'immune complex' intends the combination formed when an antibody binds to an epitope on an antigen.

The terms E1 and E2 as used herein are fully described in WO 96/04385 of which the content is incorporated by reference in the present description.

The term 'purified' as applied to proteins herein refers to a composition wherein the desired protein comprises at least 35 % of the total protein component in the composition. The desired protein preferably comprises at least 40%, more preferably at least about 50 %, more preferably at least about 60%, still more preferably at least about 70%, even more preferably at least about 80%, even more preferably at least about 85 %, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' HCV protein intends an HCV protein composition that is at least 35% pure.

The term 'essentially purified proteins' refers to proteins purified such that they can be used for in vitro diagnostic methods and as a therapeutic compound. These proteins are substantially free from cellular proteins or DNA, vector-derived proteins or DNA, or other HCV viral components. Usually these proteins are purified to homogeneity (at least 80 % pure, preferably, 85%, more preferably, 90%, more preferably 95%, more preferably 97%, more preferably 98%, more preferably 99 %, even more preferably 99.5%, and most preferably the contaminating proteins should be undetectable by conventional methods like SDS-PAGE and silver staining.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Klyveromyces, Pichia* (e.g. *Pichia pastoris*), *Hansenula* (e.g. *Hansenula polymorpha*), *Yarowia, Schwanniomyces, Zygosaccharomyces* and the like. *Saccharomyces cerevisiae, S. carlsbergensis* and *K. lactis* are the most commonly used yeast hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, and may include enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons in the reading frame selected; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, viral RNA. DNA (including cDNA), and recombinant polynucleotide sequences.

As used herein. 'epitope' or 'antigenic determinant' means an amino acid sequence that is immunoreactive. Generally an epitope consists of at least 3 to 4 amino acids, and more usually, consists of at least 5 or 6 amino acids, sometimes the epitope consists of about 7 to 8, or even about 10 amino acids. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to genotypes 1a, 1b, 1c, 1d, 1e, 1f, 2a, 2b, 2c, 2d, 2e, 2f, 2g, 2h, 2i, 3a, 3b, 3c, 3d, 3e, 3f, 3g, 4a, 4b, 4c, 4d, 4e, 4f, 4g, 4h, 4i, 4j, 4k, 4l, 5a, 5b, 6a, 6b, 6c, 7a, 7b, 7c, 8a, 8b, 9a, 9b, 10a, 11a, 12a or any other newly defined HCV (sub)type. It is to be understood that the amino acids constituting the epitope need not be part of a linear sequence, but may be interspersed by one or more series of any number of amino acids, thus forming a conformational epitope.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against HCV, whether partial or complete. A vaccine may also be useful for treatment of an individual, in which case it is called a therapeutic vaccine.

The term 'therapeutic' refers to a composition capable of treating HCV infection.

The term 'effective amount' refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment as defined above. The exact amount necessary will vary according to the application.

The term 'antibody' refers to polyclonal or monoclonal antibodies. The term 'monoclonal antibody' refers to an antibody composition having a homogeneous antibody population. The term is not limited regarding the species or source of the antibody, nor is it intended to be limited by the manner in which it is made. It should be noted that also humanized antibodies, single chain antibody or any other fragment thereof which has largely retained the specificity of said antibody are covered by the present invention.

As used herein, the term 'humanized antibody' means that at least a portion of the framework regions of an immunoglobulin are derived from human immunoglobulin sequences.

As used herein, the term 'single chain antibody' refers to antibodies prepared by determining the binding domains (both heavy and light chains) of a binding antibody, and supplying a linking moiety which permits preservation of the binding function.

As used herein, the term 'fragments (of antibodies)' refers to $F_{ab}$, $F_{(ab)2}$, $F_v$, and other fragments which retain the antigen binding function and specificity of the parent antibody.

AIMS OF THE INVENTION

It is an aim of the present invention to provide improved HCV diagnostic assay components and therapeutic proteins.

More particularly it is an aim of the present invention to provide improved HCV NS3 protein preparations for use in HCV antibody diagnosis and/or HCV treatment.

It is further an aim of the present invention to provide a method for increasing the reactivity of HCV antibodies with recombinant or synthetic NS3 helicase protein or part thereof present on a solid phase.

It is also an aim of the present invention to provide a novel method for purifying cysteine containing recombinant proteins, more particularly recombinant HCV proteins.

It is also an aim of the present invention to provide new HCV NS3 protein encoding sequences.

It is also an aim of the present invention to provide new HCV NS3 protein encoding sequences of which the product does not react with falsly positive HCV samples.

It is also an aim of the present invention to provide a method for detecting the nucleic acids of the invention.

It is also an aim of the present invention to provide probes and primers for the detection of the nucleic acids of the invention.

It is also an aim of the present invention to provide a diagnositic kit for the detection of the nucleic acids of the invention.

It is another aim of the present invention to provide new HCV NS3 polypeptides.

It is another aim of the present invention to provide new HCV NS3 polypeptides which do not react with falsly positive HCV samples.

It is another aim of the present invention to provide a pharmaceutical composition to prevent or treat HCV infection.

It is another aim of the present invention to provide a method for the detection of the polypeptides of the invention.

It is another aim of the present invention to provide antibodies to the polypeptides of the present invention for use in passive immunization and/or therapy.

It is another aim of the present invention to provide a method for the production of the polypeptides of the invention.

All the aims of the present invention are considered to have been met by the embodiments as set out below.

DETAILED DESCRIPTION OF THE INVENTION

The present invention relates more particularly to a solid phase immunoassay comprising on said solid phase an antigen in the presence of a reducing agent. As is demonstrated in the Examples section the present inventors have found that the presence of a reducing agent such as DTT, besides an antigen coated to a solid phase, renders a solid phase immunassay coupled antigen much more reactive with antibodies directed to said antigen. Also in solution, the antigen is rendered more reactive by reduction.

A reducing agent according to the present invention is any agent which achieves reduction of S—S disulfide bridges. Reduction of the 'S—S' disulfide bridges is a chemical reaction whereby the disulfides are reduced to thiol (—SH). The disulfide bridge breaking agents and methods disclosed in WO 96/04385 are hereby incorporated by reference in the present description. 'S—S' Reduction can be obtained by (1) enzymatic cascade pathways or by (2) reducing compounds. Enzymes like thioredoxin, glutaredoxin are known to be involved in the in vivo reduction of disulfides and have also been shown to be effective in reducing 'S—S' bridges in vitro. Disulfide bonds are rapidly cleaved by reduced thioredoxin at pH 7.0, with an apparent second order rate that is around $10^4$ times larger than the corresponding rate constant for the reaction with DTT. The reduction kinetic can be dramatically increased by preincubation the protein solution with 1 mM DTT or dihydrolipoamide (Holmgren, 1979).

Thiol compounds able to reduce protein disulfide bridges are for instance Dithiothreitol (DTT), Dithioerythritol (DTE), β-mercaptoethanol, thiocarbamates, bis(2-mercaptoethyl) sulfone and N,N'-bis(mercaptoacetyl)hydrazine, and sodium-dichionite.

Reducing agents without thiol groups like ascorbate or stannous chloride ($SnCl_2$), which have been shown to be very useful in the reduction of disulfide bridges in monoclonal antibodies (Thakur et al., 1991), may also be used for the reduction of NS3. Sodium borohydride treatment has been shown to be effective for the reduction of disulfide bridges in peptides (Gailit, 1993). Tris(2-carboxyethyl)phosphine (TCEP) is able to reduce disulfides at low pH (Burns et al., 1991). Selenol catalyses the reduction of disulfide to thiols when DTT or sodium borohydride is used as reductant. Selenocysteamine, a commercially available diselenide, was used as precursor of the catalyst (Singh and Kats, 1995).

The present invention relates more particularly to a method for producing an immunoassay as defined above wherein said reducing agent is added to said solid phase during the steps of coating, blocking and/or fixation of said antigen to said solid phase.

The present invention also relates to a method for carrying out an immunoassay as defined above wherein said reducing agent is added during the step of pretreatment of the solid phase.

Coating conditions can vary widely as known by the skilled person and involves applying to a solid phase the protein and allowing a reaction to occur resulting in the binding of the protein to the solid phase. Binding can be, but is not restricted to, covalently hydrophobic or ionic bonds, Van Der Waels forces or hydrogen bridges. Different buffers known by the skilled man may be used for this step, including but not limited to carbamate and phosphate buffers.

Blocking can occur via any method known in the art and can for instance also be performed using albumin, serum proteins, polyvinylpyrolidone (PVP), detergents, gelatines, polyvinylalcohol (PVA) or caseïne.

Fixation can occur according to any method known in the art.

Further examples of blocking, fixation and coating conditions are given in the Examples section.

The present invention relates even more particularly to a method as defined above wherein said reducing agent is added to said solid phase during the step of coating of the antigen to the solid phase. Examples of coating buffers are given in the Examples section. All other known coating buffers known in the art also form part of the present disclosure.

The present invention relates also to a method as defined above, wherein said reducing agent is added to said solid phase during the step of blocking said solid phase, comprising the antigen which had been applied thereto in the presence or absence of a reducing agent. Examples of blocking buffers are given in the Examples section. All other known blocking buffers known in the art also form part of the present disclosure.

The present invention relates also to a method as defined above, wherein said reducing agent is added to said solid phase during the step of fixation of the coated antigen to said solid phase comprising the antigen which had been applied thereto in the presence or absence of a reducing agent. The fixation step may also have been preceded by a blocking step in the presence or absence of a reducing agent. Examples of fixation buffers are given in the Examples section. All other known fixation buffers known in the art also form part of the present disclosure.

The present invention also relates to a method for carrying out an immunoassay as defined above wherein said reducing agent is added during the step of pretreatment of the solid phase before addition of the sample. Pretreatment of the plates can be done with plates that have been treated with a reducing agent in the coating, blocking and/or fixation step or with plates that have not been previously treated with a reducing agent.

Finally, the reducing agent may also be added during any further steps carried out in enzyme immunoassays, as part of the present invention, possibly after application of a reducing agent in one or more of the above 4 steps of coating, blocking, fixation and/or pretreatment. Such further steps include but are not limited to incubation the antibodies, detecting bound antibodies and color development.

The present invention relates preferably to a method as defined above wherein said reducing agent is DTT, DTE or TCEP.

The present invention relates also to a method as defined above wherein said reducing agent is used in a concentration range of 0.1 mM to 1 M. more particularly from 0.5 mM to 500 mM, even more particularly from 1 mM to 250 mM. most particularly from 1 to 50 mM. Some applications may require ranges from 0.5 to 50 mM, 1 to 30 mM. 2 to 20 mM, 5 to 15 mM, or about 10 mM reducing agent. Other applications require DTT concentrations of 50-500 mM, 100-300 mM or 200 mM. DTT is particularly preferred as a reducing agent.

The present invention also relates to a method as defined above wherein said antigen is an HCV NS3 protein. More particularly an HCV NS3 helicase. Also preferred is an HCV envelope protein such as E1 and/or E2 protein. Also any other protein known in the art may react better with antibodies against said protein when the protein is added to the solid phase in the presence of DTT, or treated with DTT thereafter.

The present invention also relates to a method as described above wherein said solid phase immunoassay comprises a combination of antigens of different aetiological agents or phenotypically linked conditions.

The present invention also relates to a solid phase immunoassay produced by a method as defined above. More particularly, a kit containing at least a solid phase such as a microtiterplate, a membrane strip or silicon chip which contains an antigen in the presence of a reducing agent.

More particularly, the present invention relates to an ELISA produced by a method as defined above.

In a preferred embodiment, the present invention relates to an ELISA produced by a method as defined above wherein said reducing agent is preferably added in the coating and/or fixation steps. In one preferred embodiment, the reducing agent can be applied in the coating step. In another preferred embodiment, the reducing agent can be applied in the fixation step. In a particularly preferred embodiment the reducing agent is added in both the coating and the fixation step.

In another preferred embodiment, the present invention relates to an ELISA produced by a method as defined above wherein said reducing agent is added during pretreatment of the plates before addition of the sample. Pretreatment of the plates can be done with plates that have been treated with a reducing agent in the coating and/or fixation step or with plates that have not been previously treated with a reducing agent. The reducing agent may also be added during any further steps carried out in enzyme immunoassays. Such further steps include but are not limited to incubation the antibodies, detecting bound antibodies and color development.

The present invention also relates to an Line Immunoassay (LIA) produced by a method as defined above.

In a preferred embodiment, the present invention relates to a Line Immunoassay (LIA) produced by a method as defined above wherein said reducing agent is preferably added in the blocking step and/or washing step. The reducing agent may also be added during any further steps in producing or carrying out the enzyme immunoassays. Such further steps include but are not limited to fixation, pretreatment, incubation the antibodies, detecting bound antibodies and color development.

The present invention also relates to a QUICK assay produced by a method as defined above.

In a preferred embodiment, the present invention relates to a QUICK assay produced by a method as defined above wherein said reducing agent is preferably added during the coating of the antigen onto the strip,.The QUICK assay is a lateral flow assay in which the antigens are coated onto the strips by spaying. In this assay, the reducing agent is preferably added to the spraysolution. The reducing agent may also be added during any further steps in producing or carrying out the enzyme immunoassays. Such further steps include but are not limited to blocking, fixation, pretreatment, incubation the antibodies, detecting bound antibodies and color development.

The present invention also relates to the use of an assay as defined above for in vitro diagnosis of antibodies raised against an antigen as defined above.

The present invention also relates to an HCV NS3 protein treated by a method comprising the steps of sulphonation and subsequent desulphonation.

Sulphonation and desulphonation is a reaction whereby —SO$_3$ groups are introduced or removed respectively from the protein.

Sulphonation is defined as a process where thiolgroups (SH) on proteins (R) and disulphide bonds are converted to S-Sulphonates, according to the following reactions:

$$RSH \rightarrow RS\!-\!SO_3^- \quad (1)$$

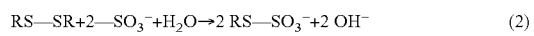

$$RS\!-\!SR + 2\!-\!SO_3^- + H_2O \rightarrow 2\,RS\!-\!SO_3^- + 2\,OH^- \quad (2)$$

The products of the reactions are S-Sulphoproteins which are usually stable at neutral pH. Reaction (1) can be obtained by incubation the protein solution with tetrathionate at pH>7 (Inglis and Liu, 1970). Reaction (2) proceeds to completion in the presence of copper ions (Cole, 1967). Chan (1968) has shown that treatment of protein with sodium sulfite and catalytic amounts of cysteine in the presence of oxygen gives sulpho-proteins.

Desulfonation can be obtained (1) by an excess of competitive —SH (thiol) groups, (2) by reducing agents or (3) by incubation in non-neutral pH conditions.

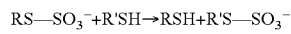

$$RS\!-\!SO_3^- + R'SH \rightarrow RSH + R'S\!-\!SO_3^-$$

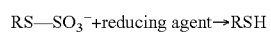

$$RS\!-\!SO_3^- + \text{reducing agent} \rightarrow RSH$$

Competitive thiol groups may be obtained from low molecular weight compounds or from proteinacous —SH groups.

Examples of mono- or dithiol containing compounds are: cysteine, cysteamine, reduced gluthation, N-acetyl cysteine, homocysteine, β-mercaptoethanol, thiocarbamates, bis(2-mercaptoethyl)sulphone (BMS) and N,N'-bis(mercaptoacetyl)hydrazine (BMH), 5,5'-dithiobis-(2-nitrobenzoic acid) (DTNB or Elman's reagent), Dithiotreitol (DTT) and Dithioerythrithiol (DTE).

The present invention relates to an HCV NS3 protein defined above which is additionally treated with zwitterionic detergent. Empigen is also known as n-dodecyl-N,N-dimethylglycine and is particularly preferred example of a zwitterionic detergent. Other suitable detergents are known by the skilled man and are reviewed also in WO96/04385.

The present invention further relates to a method for purifying a cysteine containing, recombinantly expressed protein, comprising at least 2, preferably 3 or 4, and even more preferably, all of the following steps:
(a) sulphonation of a lysate from recombinant host cells or lysis of recombinant host cells in the presence of guanidinium chloride (preferably 6 M Gu.HCl) and sulphonation of the cell lysate,
(b) treatment with a zwitterionic detergent, preferably after removal of the cell debris,
(c) purification of the sulphonated recombinant protein, or purification of the sulphonated recombinant protein with subsequent removal of the zwitterionic detergent, with said purification being preferably chromatography, more preferably a Ni-IMAC chromatography with said recombinant protein being a His-tagged recombinant protein,
(d) desulphonation of the sulphonated recombinant protein, preferably with a molar excess of a reducing agent such as DTT,
(e) storage in the presence of a molar excess of DTT.

Empigen is a particularly preferred example of a zwitterionic detergent. Inclusion of such a zwitterionic detergent and DTT was found to improve the purification protocol for HCV NS3 helicase and HCV envelope proteins.

The present invention also relates to an HCV polynucleic acid encoding an HCV NS3 polyprotein as shown in FIG. 1 (SEQ ID NOs 3-18) or a unique part of an HCV polynucleic acid having a sequence as represented in FIGS. 2-1, 3-1, 4-1, 5-1, 6-1, 7-1, and 8-1 (SEQ ID NOs 19, 21, 23, 25, 27, 29 and 31).

The present invention also relates to an HCV polynucleic acid as defined above characterized in FIGS. 2-1, 3-1, 4-1, 5-1, 6-1, 7-1, and 8-1 and by the fact that its does not react with false positive HCV samples, or a part thereof which encodes NS3 epitopes which do not react with false positive HCV samples. It was particularly surprising that the proteins coded by the clones represented by SEQ ID NOs 19, 21, 23, 25, 27, 29 and 31 have the property of not reacting with false positive HCV samples, yet they were able to react with most of the known NS3 antibody-positive samples after DTT treatement.

The present invention further relates to a recombinant vector comprising a polynucleic acid as described.

The present invention further relates to a host cell comprising a vector of the invention.

The present invention furhter relates to a method for detecting a nucleic acid of the invention. This detection method can be any method known in the art such as described in detail in WO 96/13590 to Maertens & Stuyver.

More particularly, the present invention relates to a method for detecting a nucleic acid of the invention comprising:
contacting said nucleic acid with a probe;
determining the complex formed between said nucleic acid and said probe.

In accordance, the present invention relates to an isolated nucleic acid as described above or a fragment thereof for use as a probe or a primer.

The present invention further relates to a diagnostic kit for the detection of a nucleic acid sequence as described above, comprising at least one primer and/or at least one probe according to the invention. For a detailed description to an overview of these applications reference is made to WO 96/13590.

In addition to the reactivity gained by reduction, the NS3 reactivity is also severely determined by the sequence of the NS3 antigen.

The present invention therefore also relates to an HCV polypeptide having part or all of the amino acid sequences as shown in FIGS. 1, 2-2, 3-2, 4-2, 5-2, 6-2, 7-2 and 8-2 (SEQ ID NOs 20, 22, 24, 26, 28, 30, 3)).The present invention also relates to an HCV NS3 helicase protein as depicted in FIG. 1 (SEQ ID NOs 1-18) or an unique part thereof.

The present invention also relates to an HCV NS3 helicase protein or part thereof containing either S1200, A1218, A1384, P1407, V1412, P1424, or F1444, or a combination of these amino acids with any of the following amino acids L1201, S1222, I1274, S1289, T1321, A1323, T1369, L1382, V1408, A1409, or F1410. Said numbering is according to the commonly accepted HCV amino acid numbering system.

The present invention further relates to a pharmaceutical composition comprising a polypeptide of the invention or any functionally equivalent variant or fragment thereof. The terms "a pharmaceutical composition" relates to a composition or medicament (both terms can be used interchangeably) comprising a polypeptide of the present invention and a pharmaceutically acceptable carrier or excipient (both terms can be used interchangeably). This pharmaceutical composition can be used as a medicament. This pharmaceutical composition can be used as a medicament for the treatment or prevention of HCV infection. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The "pharmaceutical composition" or "medicament" may be administered by any suitable method within the knowledge of the skilled man. The preferred route of administration is parenterally or a vaccine. In parental or vaccine administration, the medicament of this invention will be formulated in a unit dosage injectable form such as a solution, suspension or emulsion, in association with the pharmaceutically acceptable excipients as defined above. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of NS3 and/or E1 and/or E2 and/or E1/E2 single or specific oligomeric envelope proteins for prophylaxis of HCV disease are 0.01 to 1000 µg/dose, preferably 0.1 to 100 µg/dose, more preferably 1 to 50 µg/dose. Several doses may be needed per individual in order to achieve a sufficient immune response and subsequent protection against HCV disease. In the case of a therapeutic vaccine, the number of required doses may amount to more than 10. Continuous infusion may also be used. If so, the medicament may be infused at a dose between 5 and 20 µg/kg/minute, more preferably between 7 and 15 µg/kg/minute. It should also be clear that the pharmaceutical composition of the present invention may comprise a functionally equivalent variant or fragment of the sequences given by SEQ ID NOs 3-18, 20, 22, 24, 26, 28, 30, 32. The latter terms refer to a molecule which contains the full protein sequence of the polypeptide of the invention or part of the protein sequence of the polypeptide of the invention, to which certain modifications have been applied, and which retains all or part of the biological properties of the polypeptide of the invention. Such modifications include but are not limited to the addition of polysaccharide chains, the addition of certain chemical groups, the addition of lipid moieties, the fusion with other peptide or protein sequences and the formation of intramolecular cross-links.

The present invention also relates to an immunoassay comprising an HCV polypeptide as defined above. Said immunoassay can be of any type of format known in the art (see for instance WO 96/13590 and Coligan et al. 1992). In particular, the present invention relates to a method for detecting a polypeptide of the invention comprising:

contacting said polypeptide with a ligand binding to said polypeptide;
determining the complex formed between said polypeptide and said ligand.

In accordance the present invention also relates to a ligand binding to a polypeptide according of the invention. The term "a ligand" refers to any molecule able to bind the polypeptides of the present invention. The latter term specifically refers to polyclonal and/or monoclonal antibodies specifically raised (by any method known in the art) against the polypeptides of the present invention and also encompasses any antibody-like, and other, constructs as described in detail in EP 97870092.0 to Lorré et al. Such antibodies may be very useful for the detection of antigen in biological fluids. Detection of antigen can be done by any immunoassay known in the art such as assays which utilize biotin and avidin or streptavidin, ELISA's and immunoprecipitation, immunohistchemical techiques and agglutination assays. A detailed description of these assays is given in WO 96/13590 which is hereby incorporated by reference.

Furthermore, said antibodies may be very useful for therapy of HCV or other diseases and may therefore be humanized if generated in a non-human host. In accordance, the present invention relates to compositions of these antibodies in a pharmaceutical acceptable excipient, for use as a medicament.

The present invention also relates to any method for producing and using said polyproteins of the invention. Methods for producing and using HCV polyproteins are disclosed in WO 96/13590. Said uses include not only diagnostic uses but also therapeutic and prophylactic uses. The NS3 proteins of the invention are also particularly suited to be incorporated in vaccine compositions. Said vaccine composition may contain, besides the active ingredient, any type of adjuvant known in the art. The contents of WO 96/13590 are hereby incorporated by reference in the present description. The NS3 proteins of the present invention may also be used in any application where it is applicable to use an NS3 helicase, such as for drug screening purposes.

FIGURE LEGENDS

FIG. 1. Amino acid sequence of HCV NS3 clones isolated from HCV subtype 1a and 1b infected sera.

FIG. 2-1. DNA coding sequence of the mTNFH6NS3 clone 19b fusion protein. Sequence depicted in bold is non-NS3 sequence. This sequence encodes the MT-NF fusionpartner, the hexahistidine tag and part of the multilinker.

FIG. 2-2. Amino Acid sequence of the mTNFH6NS3 clone 19b fusionprotein. Sequence depicted in bold is non-NS3 sequence. This sequence contains the mTNF fusionpartner, the hexahistidine tag and part of the multilinker.

FIG. 3-1. DNA coding sequence of the mTNFH6NS3 clone B9 fusionprotein. Sequence depicted in bold is non-NS3 sequence. This sequence encodes the mTNF fusionpartner, the hexahistidine tag and part of the multilinker.

FIG. 3-2. Amino Acid sequence of the mTNFH6NS3 clone B9 fusionprotein. Sequence depicted in bold is non-NS3 sequence. This sequence encodes the mTNF fusionpartner, the hexahistidine tag and part of the multilinker.

FIG. 4-1. DNA coding sequence of the mTNFH6NS3 Type 3a clone 21 fusionprotein. Sequence depicted in bold is non-NS3 sequence. This sequence encodes the mTNF fusionpartner, the hexahistidine tag and part of the multilinker.

FIG. 4-2. Amino Acid sequence of the mTNFH6NS3 Type 3a clone 21 fusionprotein. Sequence depicted in bold is non-NS3 sequence. This sequence encodes the mTNF fusionpartner, the hexahistidine tag and part of the multilinker.

FIG. 5-1. DNA coding sequence of the mTNFH6NS3 Type 3a clone 32 fusionprotein. Sequence depicted in bold is non-NS3 sequence. This sequence encodes the mTNF fusionpartner, the hexahistidine tag and part of the multilinker.

FIG. 5-2. Amino Acid sequence of the mTNFH6NS3 Type 3a clone 32 fusionprotein. Sequence depicted in bold is non-NS3 sequence. This sequence encodes the mTNF fusionpartner, the hexahistidine tag and part of the multilinker.

FIG. 6-1. DNA coding sequence of the mTNFH6NS3 Type 2a fusionprotein. Sequence depicted in bold is non-NS3 sequence. This sequence encodes the mTNF fusionpartner, the hexahistidine tag and part of the multilinker.

FIG. 6-2. Amino Acid sequence of the mTNFH6NS3 Type 2a fusionprotein. Sequence depicted in bold is non-NS3 sequence. This sequence encodes the mTNF fusionpartner, the hexahistidine tag and part of the multilinker.

FIG. 7-1. DNA coding sequence of the mTNFH6NS3 Type 2b fusionprotein. Sequence depicted in bold is non-NS3 sequence. This sequence encodes the mTNF fusionpartner, the hexahistidine tag and part of the multilinker.

FIG. 7-2. Amino Acid sequence of the mTNFH6NS3 Type 2b fusionprotein. Sequence depicted in bold is non-NS3 sequence. This sequence encodes the mTNF fusionpartner, the hexahistidine tag and part of the multilinker.

FIG. 8-1. DNA coding sequence of the mTNFH6NS3 Type 2c fusionprotein. Sequence depicted in bold is non-NS3 sequence. This sequence encodes the mTNF fusionpartner, the hexahistidine tag and part of the multilinker.

FIG. 8-2. Amino Acid sequence of the mTNFH6NS3 Type 2c fusionprotein. Sequence depicted in bold is non-NS3 sequence. This sequence encodes the mTNF fusionpartner, the hexahistidine tag and part of the multilinker.

EXAMPLES

Example 1

Expression of HCV NS3 Type 1b Clone 19b in *E. coli*

1.1 Cloning of the HCV NS3 Type 1b Clones 19a and 19b Genes

The NS3 helicase domain (amino acids 1188-1465) was amplified by RT-PCR from HCV subtype 1b serum IG8309 (Innogenetics, Gnent, Belgium) using synthetic oligonucleotide primers HCPr59 (5'-GGGCCCCACCATGGGGGT-TGCGAAGGCGGTGGACTT-3') (SEQ ID NO 1) and HCPr60 (5'-CTATTAGCTGAAGTCGACTGTCTGGGT-GACAGCA-3') (SEQ ID NO 2). This yielded a PCR fragment 19 which was cloned into *E. coli*. The sense primer HCPr59 introduces an ApaI restriction site which includes an artifical methionine. Antisense oligonucleotide HCPr60 introduces a stopcodon after aa 1465. The PCR fragment was subsequently cut with ApaI and the resulting 833 bp ApaI fragment was cloned in the ApaI-cut expressionvector pmT-NFHRP (Innogenetics, Ghent, Belgium). Four hepatitis C clones (HCCl) were sequenced: HCCl19a and HCCl19b (see deduced amino acid sequence given in FIG. 1 and FIG. 2-2). Clone HCCl19b (pmTNFHRPHCCl19b) was retained for further subcloning.

1.2 Construction of the Expression Plasmid pEmTNFMPHHCCl19b

Starting from vector pmTNFHRPHCCl19b the NS3 clone 19b coding sequence was isolated as a 900 bp NcoI fragment and inserted into the NcoI-cut expressionvector pEmTNT-MPH (Innogenetics, Ghent, Belgium) resulting in vector pEmTNFMPHHCCl19b. This plasmid expresses HCV NS3 clone 19b as an N-terminal fusionprotein with the N-terminal 25 aa of murine TNF followed by a hexahistidine purification tag and a formic acid cleavage site (SEQ ID NOs 19 and 20; FIG. 2).

1.3 Expression of HCV NS3 Clone 19b in *E. coli*

*E. coli* strain MC1061(pAcI) cells (Wertman et al., 1986) were transformed with plasmid pEmTNFMPHHCCl19b MC1061 (pAcI) cells harboring pEmTNFMPHHCCl19b were grown overnight in Luria Broth (LB) supplemented with 10 µg/ml tetracycline at 28° C. Cultures were diluted 20 times in fresh LB, then grown at 28° C. to an $OD_{600}$ of 0.2, after which the temperature was raised to 42° C. At 2 to 3 hours post-induction, the cells were harvested. Expression of the HCV NS3 clone 19b fusion protein was analysed by western blotting using specific monoclonal antibodies and HCV positive human sera.

Example 2

Expression of HCV NS3 Clone B9 in *E. coli*

2.1 Cloning of the HCV NS3 Type 1a Clone B9 Gene

The NS3 helicase domain (amino-acids 1188-1465) was amplfied by RT-PCR from HCV subtype 1a serum IG21054 (Innogenetics, Ghent, Belgium) using synthetic oligonucleotide primers HCPr59 (5'-GGGCCCCACCATGGGGGT-TGCGAAGGCGGTGGACTT-3') (SEQ ID NO 1) and HCPr60 (5'-CTATTAGCTGAAAGTCGACTGTCTGGGT-GACAGCA-3') (SEQ ID NO 2). This yielded a PCR fragment B which was cloned into *E. coli*. The sense primer HCPr59 introduces an ApaI restriction site which includes an artifical methionine. Antisense oligonucleotide HCPr60 introduces a stopcodon after aa 1465. The PCR fragment was subsequently cloned in the pGEM-T vector (Promega, Madison, Wis., US). Four clones were sequenced: B7, B9, B 12, and B 14 (see deduced amino acid sequences in FIG. 1 and FIG. 3-2). Clone B9 (pGEMTNS3B9) was retained for further subcloning.

2.2 Construction of the Expressionplasmid pIGFH111NS3B9

Starting from vector pGEMTNS3B9, the clone B9 coding sequence was isolated as a 850 bp NcoI/SpeI blunted fragment and inserted into the NcoI/StuI cut expression vector pIGFH111 (Innogenetics, Ghent, Belgium) resulting in vector pIGFH111NS3B9. This plasmid expresses HCV NS3 clone B9 as an N-terminal fusion protein with the N-terminal 25 aa of murine TNF followed by a hexahistidine purification tag and a formic acid cleavage site (SEQ ID NOs. 21 and 22; FIG. 3).

2.3 Expression of HCV NS3 Clone B9 in *E. coli*

*E. coli* strain MC 1061(pAcI) (Wertman et al., 1986) cells were transformed with plasmid pIGFH111NS3B9. MC1061 (pAcI) cells harboring pIGFH111NS3B9 were grown overnight in Luria Broth (LB) supplemented with 10 µg/ml tetracycline at 28° C. Cultures were diluted 20 times in fresh LB, then grown at 28° C. to an $OD_{600}$ of 0.2, after which the temperature was raised to 42° C. At 2 to 3 hours post-induction, the cells were harvested. Expression of the HCV NS3 clone B9 fusion protein was analysed on Western blot using specific monoclonal antibodies and HCV positive human sera.

Example 3

Expression of HCV NS3 Type 1a Clones A26, C16, and D18 in *E. coli*

Clones A26, C16, and D18 were isolated from HCV subtype 1a infected sera IG21051, IG17790, and IG21068, respectively, in a similar way as described for clone B9 using primers HCPr59 and HCPr60. Initially, clones, A5, A26, C1, C3, C4, C12, C16, D17, D18, and D19, were cloned and sequenced (see deduced amino acid sequences given in FIG. 1). Clones A26, C16, and D18 were retained for further subcloning.

Example 4

Expression of HCV NS3 Type 3a Clones 21 and 32 in *E. coli*

4.1 Cloning of the HCV NS3 Type 3a Clones 21 and 32 Genes

The NS3 helicase domain (amino acids 1188-1465) was-amplified by RT-PCR from HCV subtype 3a sera IG21349 and IG20014 (Innogenetics, Ghent, Belgium) using synthetic oligonucleotide primers 403 (5'-GGGCCCCACCATAGGT-GTAGCAAAAGCCCTACAGTT-3') (SEQ ID NO 33) and 404 (5'-CTATTAGCTGAAGTCAACGTACTGT-TCAACAGC-3') (SEQ ID NO 34). This yielded in both cases a PCR fragment of approx. 850 bp which was subsequently subcloned in the pGEM-T vector (Promega, Madison, Wis., US). From each cloned PCR fragment several clones were sequenced but from each serum only one cloned fragment proved to be completely correct upon sequencing. This was clone 21 (pGEM-TNS3T3a.21) for serum IG21349 and clone 32 (pGEM-TNS3T3a.32) for serum IG20014 (FIGS. 4 and 5).

4.2 Construction of the Expressionplasmids pIGFH111NS3T3a.21 and pIGFH111NS3T3a.32

Starting from vectors pGEM-TNS3T3a.21 and pGEM-TNS3T3a.32, the clone 21 and 32 coding sequences were isolated as 850 bp NcoI/SalI fragments and inserted into the NcoI/SalI cut expression vector pIGFH111 (Innogenetics, Ghent, Belgium) resulting in vectors pIGFH111NS3T3a.21 and pIGFH111NS3T3a.32: respectively. These plasmids express HCV NS3 Type 3a clones 21 and 32 as N-terminal fusion proteins with the N-terminal 25 aa of murine TNF followed by a hexahistidine purification tag and a formic acid cleavage site (SEQ ID NOs 23-26; FIGS. 4 and 5).

4.3 Expression of HCV NS-3 Type 3a Clones 21 and 32 in *E. coli*

*E. coli* strain MC1061(pAcI) (Wertman et al., 1986) cells were transformed with plasmids pIGFH111NS3T3a.21 and pIGFH111NS3T3a.32, respectively. MC1061(pAcI) cells harboring pIGFH111NS3T3a.21 or pIGFH111NS3T3a.32 were grown overnight in Luria Broth (LB) supplemented with 10 µg/ml tetracycline at 28° C. Cultures were diluted 20 times in fresh LB, then grown at 28° C. to an OD600 of 0.2, after which the temperature was raised to 42° C. At 2 to 3 hours post-induction, the cells were harvested. Expression of the HCV NS3 Type 3a clones 21 and 32 fusionproteins was analysed on Western blot using specific monoclonal antibodies and HCV positive human sera.

Example 5

Expression of HCV NS3 Type 2a Clone 3 in *E. coli*

5.1 Cloning of the HCV NS3 Type 2a Clone 3 Gene

The NS3 helicase domain (amino acids 1188-1465) was amplified by RT-PCR from a HCV subtype 2a serum IG21342 (Innogenetics, Ghent, Belgium) using synthetic oligonucleotide primers 412 (5'-GGGCCCCACCATGGGCGTGGCCAAGTCCATAGACTT-3') (SEQ ID NO 35) and 413 (5'-CTATTAGCTGAAGTCTACAACTTGAGTGACCGC-3') (SEQ ID NO 36). This yields a PCR fragment of approx. 850 bp which was subsequently subcloned in the pGEM-T vector (Promega, Madison, Wis., US). Several clones were sequenced and clone 3 (pGEM-TNS3T2a) was retained for further subcloning (FIG. 6).

5.2 Construction of Expressionplasmid pIGFH111NS3T2a

Starting from vector pGEM-TNS3T2a, the clone 3 coding sequence was isolated as a 850 bp NcoI fragment and inserted into the NcoI cut expression vector pIGFH111 (Innogenetics, Ghent, Belgium) resulting in vector pIGFH111NS3T2a. This plasmid expresses HCV NS3 Type 2a clone 3 as an N-terminal fusion protein with the N-terminal 25 aa of murine TNF followed by a hexahistidine purification tag and a formic acid cleavage site (SEQ ID NOs 27 and 28; FIG. 6).

5.3 Expression of HCV NS-3 Type 2a Clone 3 in *E. coli*

*E. coli* strain MC1061(pAcI) (Wertman et al., 1986) cells were transformed with plasmid pIGFH111NS3T2a. MC1061 (pAcI) cells harbouring pIGFH111NS3T2a were grown overnight in Luria Broth (LB) supplemented with 10 μg/ml tetracycline at 28° C. Cultures were diluted 20 times in fresh LB, then grown at 28° C. to an OD600 of 0.2, after which the temperature was raised to 42° C. At 2 to 3 hours post-induction, the cells were harvested. Expression of the HCV NS3 Type 2a clone 3 fusionprotein was analysed on Western blot using specific monoclonal antibodies and HCV positive human sera.

Example 6

Expression of HCV NS3 Type 2b Clone 9 in *E. coli*

6.1 Cloning of the HCV NS3 Type 2b Clone 9 Gene

The NS3 helicase domain (amino acids 1188-1465) was amplified by RT-PCR from a HCV subtype 2b serum IG20192 (Innogenetics, Ghent, Belgium) using synthetic oligonucleotide primers 401 (5'-GGGCCCCACCATGGGCGTAGCCAAATCCATTGACTT-3') (SEQ ID NO 37) and 402 (5'-CTATTAGCTGAAGTCTACAATTTGAGAGACCGC-3') (SEQ ID NO 38). This yields a PCR fragment of approx. 850 bp which was subsequently subcloned in the pGEM-T vector (Promega, Madison, Wis., US). Several clones were sequenced and clone 9 was retained for further subcloning (FIG. 7).

6.2 Construction of Expressionplasmid pIGFH111NS3T2b

Starting from vector pGEM-TNS3T2b, the clone 9 coding sequence was isolated as a 850 bp NcoI fragment and inserted into the NcoI cut expression vector pIGFH111(Innogenetics, Ghent, Belgium) resulting in vector pIGFH111NS3T2b. This plasmid expresses HCV NS3 Type 2b clone 9 as an N-terminal fusion protein with the N-terminal 25 aa of murine TNT followed by a hexahistidine purification tag and a formic acid cleavage site (SEQ ID NOs 29-30; FIG. 7).

6.3 Expression of HCV NS-3 Type 2b Clone 9 in *E. coli*

*E. coli* strain MC1061(pAcI) cells (Wertman et al., 1986) were transformed with plasmid pIGFH111NS3T2b. MC1061 (pAcI) cells harbouring pIGFH111NS3T2b were grown overnight in Luria Broth (LB) supplemented with 10 μg/ml tetracycline at 28° C. Cultures were diluted 20 times in fresh LB, then grown at 28° C. to an OD600 of 0.2, after which the temperature was raised to 42° C. At 2 to 3 hours post-induction, the cells were harvested. Expression of the HCV NS3 Type 2b clone 9 fusionprotein was analysed on Western blot using specific monoclonal antibodies and HCV positive human sera.

Example 7

Expression of HCV NS3 Type 2c Clone 14 in *E. coli*

7.1 Cloning of the HCV NS3 Type 2c Clone 14 Gene

The NS3 helicase domain (amino acids 1188-1465) was amplified by RT-PCR from a HCV subtype 2c serum IG20031 (Innogenetics, Ghent, Belgium) using synthetic oligonucleotide primers 401 (5'-GGGCCCCACCATGGGCGTAGCCAAATCCATTGACTT-3') (SEQ ID NO 37) and 402 (5'-CTATTAGCTGAAGTCTACAATTTGAGAGACCGC-3') (SEQ ID NO 38). This yields a PCR fragment of approx. 850 bp which was subsequently subcloned in the pGEM-T vector (Promega, Madison, Wis., US). Several clones were sequenced and clone 14 (pGEM-TNS3T2c) was retained for further subcloning (FIG. 8).

7.2 Construction of Expressionplasmid pIGFH111NS3T2c

Starting from vector pGEM-TNS3T2c, the clone 14 coding sequence was isolated as a 850 bp NcoI fragment and inserted into the NcoI cut expression vector pIGFH111 (Innogenetics, Ghent. Belgium) resulting in vector pIGFH111NS3T2c. This plasmid expresses HCV NS3 Type 2c clone 14 as an N-terminal fusion protein with the N-terminal 25 aa of murine TNF followed by a hexahistidine purification tag and a formic acid cleavage site (SEQ ID NOs 31 and 32; FIG. 8).

7.3 Expression of HCV NS-3 Type 2c Clone 14 in *E. coli*

*E. coli* strain MC1061(pAcI) cells (Wertman et al., 1986) were transformed with plasmid pIGFH111NS3T2c. MC1061 (pAcI) cells harbouring PIGFH111NS3T2c were grown overnight in Luria Broth (LB) supplemented with 10 μg/ml tetracycline at 28° C. Cultures were diluted 20 times in fresh LB, then grown at 28° C. to an OD600 of 0.2, after which the temperature was raised to 42° C. At 2 to 3 hours post-induction, the cells were harvested. Expression of the HCV NS3 Type 2c clone 14 fusionprotein was analysed on Western blot using specific monoclonal antibodies and HCV positive human sera.

Example 8

Purification of the NS3 Helicase Protein Domain

Nine volumes of 8M Guanidinium hydrochloride (Gu. HCl) and 1 volume of 0.2 M $NaHPO_4$ were added to each gram equivalent of wet *E. coli* cell paste and the solution was homogenized by continuously vortexing. Solid $Na_2S_4O_6$ and $Na_2SO_3$ were added to the solution up to a final concentration of 65 and 360 mM, respectively. $CuSO_4$ (stock solution: 0.1 M in 25% $NH_3$) was added up to a final concentration of 100 μM. The solution was stirred overnight in the dark at room temperature and after incubation at −70° C. cleared by centrifugation at 4° C. (30 min, 20,000 rpm, JA20 rotor).

Empigen BB™ (Albright & Wilson Ltd., Okibury, UK) and imidazole were added to the supernatant up to a final concentration of 1% (w/v) and 20 mM, respectively. The pH was adjusted to 7.2 with 1N HCl. A sample corresponding to 3 L cell culture equivalent was loaded at 2 mL/min on a 25 mL Ni-IDA Sepharose FF (XK 16/20 column, Pharmacia, Upsala, Sweden), which had been equilibrated with buffer A containing 20 mM imidazole (buffer A: 50 mM phosphate, 6M Gu.HCl, 1% Empigen, pH 7.2). The Ni-IDA Sepharose column was washed consecutively with:

buffer A containing 20 mM imidazole
buffer A containing 35 mM imidazole
buffer A containing 50 mM imidazole
buffer B containing 50 mM imidazole (buffer B: 50 mM phosphate. 61M Gu.HCl, pH 7.2)
buffer B containing 200 mM imidazole.

Each washing step was maintained during the chromatography untill the absorbance at 280 nm reached baseline level. The column was regenerated with 50 mM EDTA, 500 mM NaCl, pH 7.0.

Fractions were analysed by SDS-PAGE using non-reducing conditions and silver staining. The mTNF-NS3 B 9fusion protein was recovered in the 200 mM imidazole elution. Western blotting using rabbit anti-human TNF (1 µg NS3/lane) and rabbit anti-E. coli (10 µg NS3/lane) showed that the NS3 exhibited a purity of over 99% after this single chromatography step.

The 200 mM imidazole elution fractions were pooled and desalted.

A 40 mL Ni-IDA eluate sample was loaded at 10 mL/min on a 300 mL Sephadex G25 column (XK 50, Pharmacia, Upsala, Sweden) which had been equilibrated pith 50 mM phosphate, 6M ureum, 1 mM EDTA, pH 7.2. 10 mL-fractions were collected and the protein concentration was determined by the micro BCA method (Pierce, Rockford, Ill., US). The protein concentration was adjusted to 500 µg/mL with the desalting buffer before desulphonation and reduction. The overall yield was 50-55 mg purified NS3 fusion protein/L culture equivalent.

Finally, DTT (stock solution: 100 mM in destined water) was added in a 100-fold molar excess versus the cysteine content in the NS3 antigen (e.g. NS3 19b contains 7 cysteins). The solution was flushed with nitrogen and incubated for 1 h at 28° C. The NS3 sample was subsequently diluted in the appropiate buffer for ELISA and LIA coating.

Example 9

NS3 Helicase Antibody Reactivity Tested in LIA

In order to test the NS3 helicase antibody reactivity, a line of 50 µg/ml NS3 antigen solution in phosphate buffered saline was applied onto nylon membrane strips. The strips were dried for at least 1 hour at a temperature between 18-24° C. and were subsequently blocked with PBS/caseine in the presence (10 mM) or absence of the reducing agent DTT. The strips were subsequently washed with PBS containing Tween 20 and either no DTT or 10 mM DTT and with water containing either no DTT or 10 mM DTT and 1 mM EDTA. The membranes were dried for 30 minutes and cut into strips for testing of different patient samples.

The results of an experiment wherein strips were incubated with the anti-HCV seroconversion panel PHV903 (Boston Biomedica Inc., Boston, US) are given in Table 1.

Example 10

NS3 Helicase Antibody Reactivity Tested in ELISA

In order to test the NS3 helicase antibody reactivity, ELISA plates were coated with the NS3 antigens purified as in Example 4 in the following way.

Microtiter plate wells were coated with NS3 protein at a concentration of 0.3 µg/ml NS3 protein in coating buffer containing 50 mM carbonate buffer, either 200 mM DTT or no DTT, and 1 mM EDTA. The microtiter plates are incubated for 18 hours at 20° C., and blocked with 300 µl of PBS/caseine buffer per well. The plates were incubated for 2 hours at 20° C. and subsequently fixed with 300 µl of fixation buffer containing either 200 mM DTT or no DTT, and 1 mM EDTA for 2 hours at 20° C.

The results are shown in Tables 2 and 3. Table 2 gives the Signal to Noise values of assays including NS3 coated and fixed with or without DTT, with the BBI seroconversion panels PHV901 to PHV912. Table 3 shows a summary of the number of days in which HCV antibodies can be detected earlier by the assay incorporating DTT. Clearly, a total number of 34 days of earlier detection in 12 HCV seroconversions can be obtained by incorporating DTT in the assay.

TABLE 1

BBI panels tested in LIA coated with HCV NS3 as described in example 9.

| PHV | +DTT[1] | −DTT[1] |
|---|---|---|
| 903-01 | − | − |
| 903-02 | − | − |
| 903-03 | +/− | − |
| 903-04 | 2 | − |
| 903-05 | 2 | +/− |
| 903-06 | 2 | +/− |
| 903-07 | 4 | 2 |
| 903-08 | 4 | 2 |

[1]−no reaction; +positive reaction; intensity ratings are given in comparison with different cut off lines sprayed onto the same strip.

TABLE 2

BBI panels tested in ELISA coated with HCV NS3 as described in example 10.

| MEMBER ID# | BLEED DATE | +DTT ($OD_{150}$) | −DTT ($OD_{150}$) |
|---|---|---|---|
| PHV901-01 | Sep. 23, 1993 | 0.1 | 0.3 |
| PHV901-02 | Nov. 27, 1993 | 0.1 | 0.3 |
| PHV901-03 | Dec. 29, 1993 | 2.0 | 2.9 |
| PHV901-04 | Dec. 31, 1993 | 2.1 | 3.0 |
| PHV901-05 | Jan. 05, 1994 | 2.2 | 3.1 |
| PHV901-06 | Jan. 07, 1994 | 2.4 | 3.2 |
| PHV901-07 | Feb. 01, 1994 | 4.1 | 6.0 |
| PHV901-08 | Feb. 09, 1994 | 3.9 | 5.9 |
| PHV901-09 | Mar. 01, 1994 | 4.0 | 7.9 |
| PHV901-10 | Mar. 08, 1994 | 4.1 | 7.8 |
| PHV901-11 | Apr. 14, 1994 | 4.2 | 8.3 |
| PHV903-01 | Feb. 07, 1992 | 0.2 | 0.2 |
| PHV903-02 | Feb. 12, 1992 | 0.9 | 0.9 |
| PHV903-03 | Feb. 14, 1992 | 1.3 | 1.6 |
| PHV903-04 | Feb. 19, 1992 | 2.5 | 2.7 |
| PHV903-05 | Feb. 21, 1992 | 2.8 | 2.8 |
| PHV903-06 | Feb. 26, 1992 | 3.2 | 4.6 |
| PHV903-07 | Feb. 28, 1992 | 3.5 | 5.4 |
| PHV903-08 | Mar. 04, 1992 | 3.5 | 4.1 |
| PHV904-01 | Apr. 18, 1995 | 0.1 | 0.2 |
| PHV904-02 | Apr. 20, 1995 | 0.1 | 0.3 |
| PHV904-03 | Apr. 25, 1995 | 0.1 | 0.2 |
| PHV904-04 | Apr. 27, 1995 | 0.1 | 0.2 |
| PHV904-05 | May 02, 1995 | 0.4 | 0.4 |
| PHV904-06 | May 09, 1995 | 0.8 | 0.5 |
| PHV904-07 | May 11, 1995 | 0.8 | 0.5 |
| PHV905-01 | Nov. 17, 1995 | 0.1 | 0.2 |
| PHV905-02 | Nov. 21, 1995 | 0.1 | 0.3 |
| PHV905-03 | Nov. 24, 1995 | 0.1 | 0.3 |
| PHV905-04 | Nov. 28, 1995 | 0.2 | 0.3 |
| PHV905-05 | Dec. 01, 1995 | 0.5 | 0.3 |
| PHV905-06 | Dec. 05, 1995 | 1.0 | 0.4 |
| PHV905-07 | Dec. 08, 1995 | 2.5 | 0.8 |

TABLE 2-continued

BBI panels tested in ELISA coated with HCV NS3 as described in example 10.

| | | | |
|---|---|---|---|
| PHV905-08 | Dec. 12, 1995 | 3.5 | 2.2 |
| PHV905-09 | Dec. 15, 1995 | 3.5 | 3.2 |

| MEMBER ID# | BLEED DATE | +DTT | −DTT |
|---|---|---|---|
| PHV907-01 | Apr. 06, 1996 | 0.1 | 0.2 |
| PHV907-02 | Apr. 10, 1996 | 0.1 | 0.2 |
| PHV907-03 | Apr. 13, 1996 | 0.1 | 0.2 |
| PHV907-04 | Apr. 19, 1996 | 3.0 | 2.2 |
| PHV907-05 | Apr. 24, 1996 | 3.7 | 4.1 |
| PHV907-06 | Apr. 27, 1996 | 3.6 | 4.1 |
| PHV907-07 | Sep. 17, 1996 | 3.9 | 7.6 |
| PHV908-01 | Jan. 26, 1996 | 0.1 | 0.1 |
| PHV908-02 | Jan. 29, 1996 | 0.1 | 0.1 |
| PHV908-03 | Jan. 31, 1996 | 0.1 | 0.1 |
| PHV908-04 | Feb. 06, 1996 | 0.1 | 0.1 |
| PHV908-05 | Feb. 08, 1996 | 0.1 | 0.1 |
| PHV908-06 | Feb. 14, 1996 | 0.2 | 0.1 |
| PHV908-07 | Feb. 20, 1996 | 1.4 | 0.2 |
| PHV908-08 | Feb. 22, 1996 | 1.6 | 0.2 |
| PHV908-09 | Feb. 27, 1996 | 1.9 | 0.2 |
| PHV908-10 | Mar. 01, 1996 | 2.3 | 0.2 |
| PHV908-11 | Mar. 07, 1996 | 2.3 | 0.4 |
| PHV908-12 | Mar. 11, 1996 | 2.8 | 0.5 |
| PHV908-13 | Mar. 14, 1996 | 2.8 | 0.5 |
| PHV909-01 | Jan. 28, 1996 | 0.1 | 0.4 |
| PHV909-02 | Feb. 15, 1996 | 2.3 | 5.4 |
| PHV909-03 | Feb. 17, 1996 | 2.4 | 5.3 |
| PHV910-01 | Aug. 26, 1996 | 0.1 | 0.2 |
| PHV910-02 | Aug. 30, 1996 | 0.4 | 0.2 |
| PHV910-03 | Sep. 03, 1996 | 2.7 | 3.1 |
| PHV910-04 | Sep. 06, 1996 | 3.6 | 6.4 |
| PHV910-05 | Sep. 10, 1996 | 3.9 | 8.1 |
| PHV911-01 | Oct. 30, 1996 | 0.1 | 0.2 |
| PHV911-02 | Nov. 02, 1996 | 0.1 | 0.2 |
| PHV911-03 | Nov. 13, 1996 | 2.1 | 4.0 |
| PHV911-04 | Nov. 20, 1996 | 3.6 | 7.8 |
| PHV911-05 | Nov. 23, 1996 | 3.7 | 7.7 |
| PHV912-01 | Jan. 06, 1996 | 0.2 | 0.3 |
| PHV912-02 | Jan. 10, 1996 | 0.2 | 0.2 |
| PHV912-03 | Jan. 13, 1996 | 4.5 | 9.9 |
| PHV902-01 | Feb. 10, 1992 | 0.1 | 0.2 |
| PHV902-02 | Feb. 12, 1992 | 0.1 | 0.2 |
| PHV902-03 | Feb. 17, 1992 | 0.1 | 0.3 |
| PHV902-04 | Feb. 19, 1992 | 0.3 | 0.6 |
| PHV902-05 | Feb. 24, 1992 | 2.6 | 3.9 |
| PHV902-06 | Feb. 26, 1992 | 3.1 | 5.9 |
| PHV902-07 | Mar. 02, 1992 | 3.4 | 6.5 |
| PHV906-01 | Oct. 07, 1995 | 0.5 | 0.3 |
| PHV906-02 | Oct. 09, 1995 | 0.5 | 0.4 |
| PHV906-03 | Oct. 14, 1995 | 1.6 | 0.6 |
| PHV906-04 | Oct. 17, 1995 | 1.5 | 1.2 |
| PHV906-05 | Oct. 21, 1995 | 2.2 | 3.0 |
| PHV906-06 | Oct. 24, 1995 | 2.5 | 4.5 |
| PHV906-07 | Oct. 28, 1995 | 2.9 | 5.7 |

TABLE 3

Overview of the BBI panels - numbers of days with earlier detection

| PHV | +DTT | −DTT |
|---|---|---|
| 901 | 0 | 0 |
| 902 | 0 | 0 |
| 903 | 0 | 0 |
| 904 | 0 | 0 |
| 905 | 7 | 0 |
| 906 | 3 | 0 |
| 907 | 0 | 0 |
| 908 | 24 | 0 |
| 910 | 0 | 0 |
| 911 | 0 | 0 |
| 912 | 0 | 0 |

REFERENCES

Burns, J., Butler, J., Moran, J., and Whitesides, G. (1991) Selective reduction of disulfides by tris(2-carboxyetyl) phosphine. J. Org. Chem. 56, 2648-2650.

Chan. W. (1968) A method for the complete S sulfonation of cysteine residues in proteins. Biochemistry-7, 4247-4254.

Claeys, H., Volkaerts, A., Verhaert, H., De Beenhouwer, H., and Vermylen, C. (1992) Evaluation of anti-HCV capsid indeterminate samples. The Lancet 340, 249.

Cole, R. (1967) Sulfitolysis. Meth. Enzymol. 11, 206.

Coligan, J., Kruisbeek, A., Margulis, D., Shevach, E. and Strober, W. (1992) Current protocols in immunology. Wiley Interscience.

De Beenhouwer, H., Verhaert, H., Claeys, H., and Vermylen, C. (1992) Confirmation of hepatitis C virus positive blood donors by immunoblotting and polymerase chain reaction. Vox. Sang. 63, 198-203.

Di Bisceglie, A M, Carithers, R L Jr, Gores, G J (1998) Hepatocellular carcinoma. Hepatology. 28, 1161-1165.

Gailit, J. (1993) Restoring free sulfhydryl groups in synthetic peptides. Anal. Biochem., 214, 334-335.

Holmgzren, A. (1979) Thioredoxin catalyzes the reduction of insulin disulfides by dithiothreitol and dihydrolipoamide. J. Biol. Chem. 254, 9627-9632.

Inglis, A., and Liu, T. (1970) The stability of cysteine and cystine during acid hydrolysis of proteins and peptides. J. Biol. Chem. 245, 112-116.

McFarlane, I., Smith. H., Johnson, P., Bray, G., Vergani, D., and Williams, R. (1990) Hepatitis C virus antibodies in chronic active hepatitis: pathogenic factor or false-positive result? The Lancet 335, 754-757.

Maertens, G. and Stuyver, L. (1997) Genotypes and Genetic variation of hepatitis C virus. In: Molecular Medicine of Hepatitis (Eds. Zuckerman, A. and Harrison, T.), Molecular Medical Science Series (Eds. James, K. and Morris A) John Wiley and Sons Ltd., Chichester, England, Chapter 13, pp. 183-233.

Mann, M., Bresciani, S., Puoti, M., Rodella, A., Gussago, A., Ravaggi, A., Pizzocolo, G., Albertini, A., and Cariani, E. (1994) Clinical significance of serum HCV RNA as marker of HCV infection. J. Clin. Microbiol. 32, 3008-3012.

Peeters, D., Dekeyser, F., DeLeys, R., Maertens, G., and Pollet, D. (1993) Confirmation of anti-hepatitis C virus antibodies using the INNO-LIA HCV Ab III including Core, E2/NS1, NS3, NS4, and NS5 epitopes. International Symposium on Viral Hepatitis and Liver Disease, Tokyo, abstract 413.

Pollet, D., Saman, E., Peeters, D., Warmenbol, H., Heyndricks, L., Wouters, C., Beelaert, G., van der Groen, G., and Van Heuverswyn, H. (1990) Confirmation and differentiation of antibodies to human immunodeficiency virus 1 and 2 with a strip-based assay including recombinant antigens and synthetic peptides. Clin. Chem. 37, 1700-1707.

Saito, I., Miyamura, T., Ohbayashi, A., Harada, H., Katayama, T., Kikuchi, S., Watanabe, Y., Koi, S., Onji, M., Ohta, Y., Choo, Q.-L., Houghton, M., and Kuo, G. (1990) Proc. Natl. Acad. Sci. USA 87, 6547-6549.

Singh, R., and Kats, L. (1995) Catalysis of reduction of disulfide by selenol. Anal. Biochem. 232, 86-91.

Stuyver, L., Fretz, C., Esquivel, C., Boudifa, A., Jaulmes, D., Azar, N., Lunel, F., Leroux-Roels, G., Maertens, G., and Fournel, J. (1996) HCV genotype analysis in apparently healthy anti-HCV positive Parisian blood donors. Transfusion 36, 552-558.

Thaklur, M., DeFulvio, J., Richard, M., and Park, C. (1991) Technetium-99m labeled monoclonal antibodies: evaluation of reducing agents. Nucl. Med. Biol., 18, 227- 233.

Waumans, L., Claeys, H., Verhaert H., Mertens, W., and Vermylen, C. (1993) Hepatitis C virus confirmation in blood donor screening. Vox. Sang. 64, 145-149.

Wertman K. F., Wyman A. R. and Botstein D. (1986) Host/vector interactions which affect the viability of recombinant phage lambda clones. Gene 49: 253-262.

Zaaijer, H., Vrielink, H., van Exel-Oehlers, P., Cuypers, H., and Lelie, P. (1994) Confirmation of hepatitis C infection: a comparison of five immunoblot assays. Transfusion 34, 603-607.

---

The invention claimed is:

1. A method for producing a solid phase immunoassay kit comprising an HCV NS3 protein coated to said solid phase, said method comprising performing at least one of the following steps in the presence of reducing agent:
   (i) the step of blocking of said solid phase coated with said HCV NS3 protein, and
   (ii) the step of fixation or washing of said solid phase coated with said HCV NS3 protein.

2. The method according to claim 1 further comprising producing said HCV NS3 protein by a method comprising the steps of sulphonation and subsequent desulphonation.

3. The method according to claim 1 wherein said HCV NS 3 protein comprises an HCV NS3 amino acid sequence selected from the group consisting of SEQ ID NO:3-18.

4. The method according to claim 1 wherein said HCV NS3 protein is contained in a fusion protein.

5. The method according to claim 4 wherein said fusion protein is selected from the group of amino acid sequences consisting of SEQ ID NO:20, SEQ ID NO:22, SEQ ID NO:24, SEQ ID NO:26, SEQ ID NO:28, SEQ ID NO:30 and SEQ ID NO:32.

6. The method according to claim 2 further comprising treating said HCV NS3 protein with a zwitter-ionic detergent.

7. The method according to claim 6 wherein said zwitter-ionic detergent is n-dodecyl-N,N-dimethylglycine.

8. The method according to claim 1 wherein said reducing agent is selected from DTT, DTE or TCEP.

9. The method according to claim 8 wherein said reducing agent is used in a concentration range of 0.1 mM to 1 M.

10. The method of claim 1 comprising performing the following steps in the presence of reducing agent:
    the step of coating of said solid phase with said HCV NS3 protein, and
    the step of fixation of said solid phase coated with said HCV NS3 protein.

11. The method of claim 10, further comprising performing at least one the following steps in the presence of reducing agent:
    the step of blocking of said solid phase coated with said HCV NS3 protein, and
    the step of pretreatment of said solid phase coated with said HCV NS3 protein.

12. The method of claim 1 comprising performing the following steps in the presence of reducing agent:
    the step of blocking of said solid phase coated with said HCV NS3 protein, and
    the step of washing of said solid phase coated with said HCV NS3 protein.

13. The method of claim 12, further comprising performing at least one the following steps in the presence of reducing agent:
    the step of coating of said solid phase with said HCV NS3 protein, and
    the step of pretreatment of said solid phase coated with said HCV NS3 protein.

14. The method of claim 10 or claim 11 wherein said solid phase is a solid phase of an ELISA kit.

15. The method of claim 12 or claim 13 wherein said solid phase is a solid phase of a Line ImmunoAssay kit.

16. The method of claim 1, further comprising performing the step of coating of said solid phase with said HCV NS3 protein in the presence of reducing agent.

17. The method of claim 1, further comprising performing the step of pretreatment of said solid phase coated with said HCV NS3 protein in the presence of reducing agent.

* * * * *